US008394767B2

(12) United States Patent
Dickerson et al.

(10) Patent No.: US 8,394,767 B2
(45) Date of Patent: Mar. 12, 2013

(54) METHODS OF TREATING CANCER USING THE CALCITONIN-GENE RELATED PEPTIDE ("CGRP") RECEPTOR ANTAGONIST CGRP8-37

(75) Inventors: Ian M. Dickerson, Pittsford, NY (US); Edward B. Brown, Honeoye Falls, NY (US)

(73) Assignee: University of Rochester, Rochester, NY (US)

( * ) Notice: Subject to any disclaimer, the term of this patent is extended or adjusted under 35 U.S.C. 154(b) by 0 days.

(21) Appl. No.: 12/987,876

(22) Filed: Jan. 10, 2011

(65) Prior Publication Data

US 2011/0189205 A1 Aug. 4, 2011

Related U.S. Application Data

(63) Continuation-in-part of application No. PCT/US2009/050103, filed on Jul. 9, 2009.

(60) Provisional application No. 61/079,204, filed on Jul. 9, 2008.

(51) Int. Cl.
 A61K 38/23 (2006.01)
 A61K 38/00 (2006.01)
(52) U.S. Cl. .................... 514/11.9; 530/307; 530/388.8; 424/573
(58) Field of Classification Search .................... None
See application file for complete search history.

(56) References Cited

U.S. PATENT DOCUMENTS

| 6,759,038 B2 | 7/2004 | Tan et al. | |
| 2002/0164707 A1* | 11/2002 | Adamou et al. | 435/69.1 |
| 2006/0068464 A1 | 3/2006 | Ramkrishnan | |
| 2006/0173046 A1 | 8/2006 | Bell et al. | |
| 2007/0117784 A1 | 5/2007 | Cleland et al. | |
| 2007/0259850 A1 | 11/2007 | Mercer et al. | |

FOREIGN PATENT DOCUMENTS

| WO | WO/97/41223 | * 11/1997 |
| WO | 2009/018275 A1 | 2/2009 |

OTHER PUBLICATIONS

Ittner et al., "Aspartate(69) of the Calcitonin-Like Receptor is Required for its Functional Expression Together with Receptor-Activity-Modifying Proteins 1 and -2," Biochem. Biophys. Res. Comm. 319:1203-1209 (2004).
Heroux et al., "Assembly and Signaling of CRLR and RAMP1 Complexes Assessed by BRET," Biochenn.46 (23):7022-7033 (2007) (abstract only).
Udawela et al., "A Critical Role for the Short Intracellular C Terminus in Receptor Activity-Modifying Protein Function," Mol. Pharmacol. 70(5)1750-1760 (2006).
Poyner et al., "International Union of Pharmacology. XXXII. The Mammalian Calcitonin Gene-Related Peptides, Adrenomedullin, Amylin, and Calcitonin Receptors," Pharmacol. Rev. 54(2):233-246 (2002).
Toda et al., "Neuronal System-Dependent Facilitation of Tumor Angiogenesis and Tumor Growth by Calcitonin Gene-Related Peptide," PNAS 105(36):13550-13555 (2008).
Toda et al., "Role of Calcitonin Gene-Related Peptide in Facilitation of Wound Healing and Angiogenesis," Biomed. Pharmacother. 62(6):352-359 (2008).
Ohno et al., "Roles of Calcitonin Gene-Related Peptide in Maintenance of Gastric Mucosal Integrity and in Enhancement of Ulcer Healing and Angiogenesis," Gastroenterol. 134:215-225 (2008).
International Search Report for PCT/US2009/050103 dated Dec. 30, 2009.
Written Opinion for PCT/US2009/050103 dated Dec. 30, 2009.
International Preliminary Report on Patentability for PCT/US2009/050103 dated Jan. 11, 2011.
Zhou Z., "A Study of CGRP Receptor and its Effect on the Growth of Human Pancreatic Carcinoma Cells," Zhongguo Yi Xue Ke Xue Yuan Xue Bao 15(6):427-32 (1993) (abstract only).
Evans et al., "CGRP-RCP, a Novel Protein Required for Signal Transduction at Calcitonin Gene-related Peptide and Adrenomedullin Receptors," J. Biol. Chem. 275(40):31438-443 (2000).
Zheng et al., "Calcitonin Gene-related Peptide Promotes Angiogenesis via AMP-activated Protein Kinase," Am. J. Physiol. Cell Physiol. 299:C1485-92 (2010).
Brain et al., "Vascular Actions of Calcitonin Gene-related Peptide and Adrenomedullin," Physiol. Rev. 84:903-34 (2004).

* cited by examiner

*Primary Examiner* — Elly-Gerald Stoica
(74) *Attorney, Agent, or Firm* — LeClairRyan, a Professional Corporation

(57) ABSTRACT

The present invention is directed to methods of treating cancer and preventing cancer metastasis in a subject by administering a modulator of CGRP receptor signaling. The present invention is further directed to methods of identifying novel compounds that inhibit CGRP receptor signaling, and reagents and animal models useful for the same.

3 Claims, 11 Drawing Sheets

Figures 7A-C

Alexa 488 succinimyl ester (MW 516)

CGRP (1° amines indicated) (MW 3804)

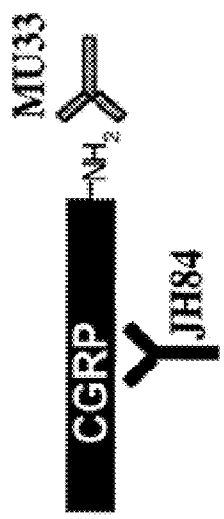
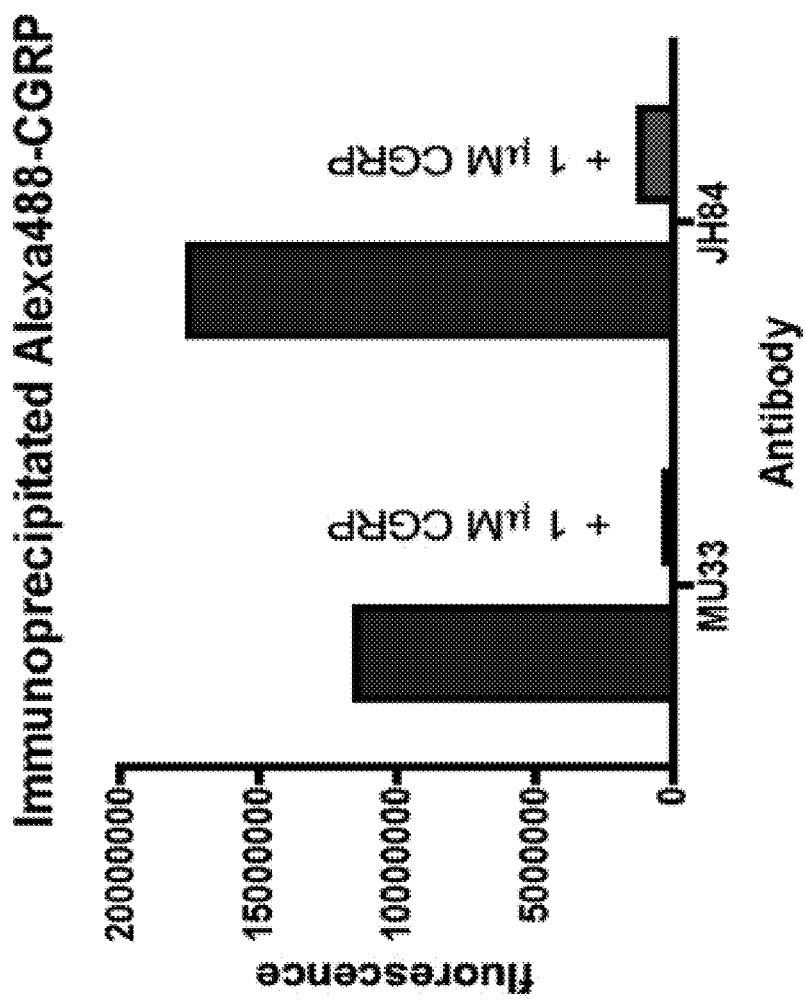
Figure 10B
Figure 10A

METHODS OF TREATING CANCER USING THE CALCITONIN-GENE RELATED PEPTIDE ("CGRP") RECEPTOR ANTAGONIST CGRP8-37

This application is a continuation-in-part of PCT/US2009/050103, filed Jul. 9, 2009, which claims the priority benefit of U.S. Provisional Patent Application Ser. No. 61/079,204, filed Jul. 9, 2008, each of which is hereby incorporated by reference in its entirety.

FIELD OF THE INVENTION

The present invention is directed to methods of treating cancer and preventing cancer metastasis by modulating calcitonin-gene related peptide (CGRP) receptor signaling. Methods of identifying compounds that modulate CGRP receptor signaling are also disclosed.

BACKGROUND OF THE INVENTION

There are currently ~2.5 million breast cancer survivors in the United States. Breast cancer affects ~180,000 new Americans annually, and kills 40,000 patients (Ries, "SEER Cancer Statistics Review 1975-2005" (eds.) (National Cancer Institute, Bethesda, 2008). The primary cause of death is due to metastasis to distant organs, including bone, liver, lungs, and brain. Although great strides have been made in the treatment of primary tumors in breast cancer, the incidence of fatal metastatic events is still very high. In particular, it is estimated that 10-15% of patients have symptomatic brain metastases (Patanaphan et al., "Breast Cancer: Metastatic Patterns and Their Prognosis," South Med J 81(9):1109-12 (1988); and Tsukada et al., "Central Nervous System Metastasis From Breast Carcinoma Autopsy Study," Cancer 52(12):2349-54 (1983)) and in as many as 30% of patients brain metastases are found on autopsy (Cho et al., "Causes of Death and Metastatic Patterns in Patients With Mammary Cancer. Tenyear Autopsy Study," Am J Clin Pathol 73(2):232-4 (1980); and Lee Y. T., "Breast Carcinoma: Pattern of Metastasis At Autopsy," J Surg Oncol 23(3):175-80 (1983)). Breast cancer is the second leading cause of CNS metastases (Lee Y. T., "Breast Carcinoma: Pattern of Metastasis At Autopsy," J Surg Oncol 23(3):175-80 (1983); Kesari et al., "Leptomeningeal Metastases," Neurol Clin 21(1):25-66 (2003); Nussbaum et al., "Brain Metastases. Histology, Multiplicity, Surgery, and Survival," Cancer 78(8):1781-8 (1996); and Zimm et al., "Intracerebral Metastases in Solid-Tumor Patients: Natural History and Results of Treatment," Cancer 48(2):384-94 (1981)), and the clinical prognosis for patients with metastases is poor, with one-year survival rates of 20% (DiStefano et al., "The Natural History of Breast Cancer Patients With Brain Metastases," Cancer 44(5):1913-8 (1979); and Engel et al., "Determinants and Prognoses of Locoregional and Distant Progression in Breast Cancer," Int J Radiat Oncol Biol Phys 55(5):1186-95 (2003)).

Treatment includes corticosteroids, radiation therapy, and surgery (Lin et al., "CNS Metastases in Breast Cancer," J Clin Oncol 22(17):3608-17 (2004)). Recent clinical treatment has focused on developing antagonists for the estrogen receptor, progesterone receptor, and human epidermal growth factor. However, approximately 25% of all patients with breast cancer lack these three receptors and do not respond to standard chemotherapy (Bauer et al., "Descriptive Analysis of Estrogen Receptor (ER)-Negative, Progesterone Receptor (PR)-Negative, and HER2-Negative Invasive Breast Cancer, the So-Called Triple-Negative Phenotype: A Population-Based Study From the California Cancer Registry," Cancer 109(9):1721-8 (2007); Carey et al., "The Triple Negative Paradox Primary Tumor Chemosensitivity of Breast Cancer Subtypes," Clin Cancer Res 13(8):2329-34 (2007); Dent et al., "Triple-Negative Breast Cancer: Clinical Features and Patterns of Recurrence," Clin Cancer Res 13(15):4429-34 (2007); and Haffty et al., "Locoregional Relapse and Distant Metastasis in Conservatively Managed Triple Negative Early-Stage Breast Cancer," J Clin Oncol 24(36):5652-7 (2006)). In addition, treatment with trastuzumab, a monoclonal antibody against the human epidermal growth factor-2 receptor, appears to be effective for combating breast cancer in the periphery but not in the central nervous system, and patients treated with trastuzumab show an increased incidence of brain metastases (Bartsch et al., "Trastuzumab Prolongs Overall Survival in Patients With Brain Metastases From Her2 Positive Breast Cancer," J Neurooncol 85(3):311-7 (2007); and Yau et al., "Incidence, Pattern and Timing of Brain Metastases Among Patients With Advanced Breast Cancer Treated With Trastuzumab," Acta Oncol 45(2):196-201 (2006)).

Additionally, aggressive tumors often exhibit regions of hypoxia (low oxygen concentration), and hypoxic tumor cells are often resistant to chemotherapy and radiation therapy (Batchelder et al., "Oxygen Dependence of the Cytotoxicity of the Enediyne Anti-Tumour Antibiotic Esperamicin A1," Br J Cancer Suppl 27:S52-6 (1996); Brizel et al., "Oxygenation of Head and Neck Cancer: Changes During Radiotherapy and Impact on Treatment Outcome," Radiother Oncol 53(2):113-7 (1999); Comerford et al., "Hypoxia-Inducible Factor-1-Dependent Regulation of the Multidrug Resistance (MDR1) Gene," Cancer Res 62(12):3387-94 (2002); Nordsmark et al., "Pretreatment Oxygenation Predicts Radiation Response in Advanced Squamous Cell Carcinoma of the Head and Neck," Radiother Oncol 41(1):31-9 (1996); and Teicher et al., "Classification of Antineoplastic Agents by Their Selective Toxicities Toward Oxygenated and Hypoxic Tumor Cells," Cancer Res 41(1):73-81 (1981)). Hypoxiaresistant breast cancer tumor cells show increased proliferation, metastasis and poor prognosis (Gruber et al., "Hypoxia-Inducible Factor 1 Alpha in High-Risk Breast Cancer: An Independent Prognostic Parameter?" Breast Cancer Res 6(3):R191-8 (2004); Schindl et al., "Overexpression of Hypoxia-Inducible Factor 1α is Associated With an Unfavorable Prognosis in Lymph Node-Positive Breast Cancer," Clin Cancer Res 8(6):1831-7 (2002); and Zhong et al., "Overexpression of Hypoxia-Inducible Factor 1α in Common Human Cancers and Their Metastases," Cancer Res 59(22):5830-5 (1999)). Consequently, inhibition of breast cancer metastasis, including metastasis to the brain, would affect lives of millions of people per year, and in the process would ease a significant economic burden on them, their families, and their caregivers, as well as society as a whole.

Malignant glioblastomas are highly aggressive tumors characterized by rapid proliferation, invasiveness, high vascularization, and resistance to apoptosis and thus most chemotherapy and radiotherapy (Schmitt C. A., "Senescence, apoptosis and Therapy—Cutting the Lifelines of Cancer," Nat Rev Cancer 3(4): 286-95 (2003). Patients generally survive less than two years from diagnosis (Curran et al., "Recursive Partitioning Analysis of Prognostic Factors in Three Radiation Therapy Oncology Group Malignant Glioma Trials," J Natl Cancer Inst 85(9): 704-10 (1993); Curran et al., "Survival Comparison of Radiosurgery-Eligible and -Ineligible Malignant Glioma Patients Treated with Hyperfractionated Radiation Therapy and Carmustine: A Report of Radiation Therapy Oncology Group 83-02," J Clin Oncol 11(5):

857-62 (1993); DeAngelis L. M., "Brain Tumors," *N Engl J Med* 344(2): 114-23 (2001)). Current treatment combines radiotherapy with temozolomide chemotherapy, which results in approximately a two year survival rate of 26% (Stupp et al., "Radiotherapy Plus Concomitant and Adjuvant Temozolomide for Glioblastoma," *N Engl J Med* 352(10): 987-96 (2005)). Recent research has focused on identifying cellular factors that promote growth and angiogenesis of gliomas in the hopes of identifying new targets for pharmacologic intervention, but none have yet shown specificity or efficacy required for therapeutic use (Wong et al., "Targeting Malignant Glioma Survival Signalling To Improve Clinical Outcomes," *J Clin Neurosci* 14(4): 301-8 (2007); and Omuro et al., "What is New in the Treatment of Gliomas?" *Curr Opin Neurol* 20(6): 704-7 (2007)).

It would be desirable to identify a new target for the treatment of breast cancer malignancies, particularly those that create secondary tumors at sites such as the brain, as well as gliomas. Likewise, identifying compounds that can be used to modulate this target are desirable for the treatment of existing breast cancer tumors and/or gliomas, and the prevention of secondary tumor formation resulting therefrom. Finally, it would be of significant benefit to develop a screening assay that can be used to identify additional compounds that can be used to treat existing breast cancer, gliomas, or secondary tumors resulting therefrom.

The present invention is directed to overcoming these and other deficiencies in the art.

SUMMARY OF THE INVENTION

A first aspect of the present invention relates to a method of treating cancer that includes administering to a patient having cancer an effective amount of an agent that modulates activity of calcitonin-gene related peptide ("CGRP") receptor, wherein said administering is effective to treat the cancer.

A second aspect of the present invention relates to a method of modifying survival of a cancerous cell that includes contacting a cancer cell with an agent that modulates activity of the CGRP receptor, wherein said contacting is effective to modulate CGRP receptor activity and either kill or inhibit growth of the cancer cell.

A third aspect of the present invention relates to a method of preventing establishment of a cancerous metastasis that includes contacting a cancer cell with an agent that modulates activity of the CGRP receptor, wherein said contacting is effective to prevent establishment of a cancerous metastasis by the cancer cell.

A fourth aspect of the present invention relates to a non-human mammal that includes tumor cells introduced into the mammal, wherein the tumor cells express the CGRP receptor and include a transgene expressing a fluorescent marker protein.

A fifth aspect of the present invention relates to a transgenic cell line that includes a transgene that expresses a dominant-negative regulator of CGRP receptor function. Preferably, the dominant-negative regulator of CGRP receptor function is under control of an inducible promoter.

A sixth aspect of the present invention relates to a method of screening compounds for inhibition of CGRP receptor function. This method includes the steps of contacting a eukaryotic cell that expresses the CGRP receptor with a test agent; and determining the effect, if any, of the test agent on CGRP receptor function, or the effect on protein-protein interactions between calcitonin-like receptor ("CLR") and receptor activity modifying protein type 1 ("RAMP1"), CLR and receptor component protein ("RCP"), or RAMP1 and RCP.

A seventh aspect of the present invention relates to a purified, fluorescent CGRP comprising a single fluorophore tethered to the peptide, wherein the fluorescent CGRP is capable of binding to a CGRP receptor. In one embodiment, the fluorescent CGRP consists of the CGRP and the single fluorophore tethered to residue $Lys^{24}$.

The present invention relates to the identification of the CGRP receptor (and its component protein subunits) as a novel target for cancer, particularly breast cancer and glioma, and malignant secondary tumors resulting therefrom. The examples of the present application identify RCP as the primary component of the CGRP receptor that is differentially upregulated in MDA-MB-231 BR cells under hypoxic conditions, and that these same cells proliferate under conditions of hypoxia and CGRP receptor stimulation whereas MDA-MB-231 cells do not. Rat CNS1 glioma cells were also shown to proliferate in the presence of CGRP receptor stimulation. These data explain why some breast cancers metastasize to the brain and proliferate, while others do not. These data explain why some tumors can proliferate under hypoxic conditions. The examples also identify the second cytoplasmic domain of CLR as a drug target, because a peptide fragment comprising this second cytoplasmic loop constitutes a dominant-negative regulator that blocks interaction between CLR and RCP, thus inhibiting CGRP signaling and proliferation of cancer cells.

BRIEF DESCRIPTION OF THE DRAWINGS

FIG. 7A is a schematic illustration showing that the second intracellular loop of CLR was cloned as a fusion protein with enhanced green fluorescent protein (EGFP). FIG. 7B shows the results obtained following loop2-EGFP fusion protein (L2/EGFP) was transfection into NIH3T3 cells, and GFP protein immunoprecipitation. The immunoprecipitate was separated by SDS-PAGE and probed with an antibody directed against RCP. RCP co-immunoprecipitated with the L2/EGFP fusion protein (lanes 5, 6) indicating an interaction between RCP and the second intracellular loop of CLR. FIG. 7C is a graph showing that when L2/EGFP protein was transfected into NIH3T3 cells, expression of the L2/EGFP inhibited signaling at the CGRP receptor.

FIG. 9A shows the absorbance (210 nm) of an HPLC run, with both unlabeled and labeled CGRP derivatives identified. FIG. 9B is a magnified time-scale of FIG. 9A, showing the purified FL-CGRP as detected by absorbance at 210 nm and by fluorescence. Offset for fluorescence from absorbance due to volume of tubing from UV detector to fraction.

FIGS. 10A-B illustrate the immunoprecipitation of FL-CGRP using anti-CGRP antibodies JH84 and MU33. FIG. 10B schematically illustrates the binding sites of these antibodies.

DETAILED DESCRIPTION OF THE INVENTION

The present invention relates to a method of treating cancer, modifying survival of cancer cells, and, importantly, preventing establishment of a cancerous metastasis (i.e., a secondary tumor). As used herein, the treatment of cancer includes, without limitation, slowing tumor growth, halting tumor growth, reversing tumor growth, eliminating a tumor, inhibiting angiogenesis within a tumor, inhibiting lymphangiogenesis within a tumor, preventing metastasis, and/or enhancing immune response against a tumor.

The types of cancer to be treated in accordance with the present invention are those cancers that are characterized by cancer cell expression of the CGRP receptor or any one of the CGRP receptor proteins. In particular, those cancers that may proliferate in response to CGRP, induce angiogenesis in response to CGRP, induce lymphangiogenesis in response to CGRP, establish metastases in response to CGRP, and/or suppress immune cells in response to CGRP, are intended to be treated in accordance with the present invention. Exemplary cancers include, without limitation, breast, ovarian, prostate, liver, lung, colon, stomach, esophageal, glioma, and melanoma.

As identified in the examples, applicants have identified a surprising role of CGRP in two different situations, which are relevant to growth of a primary tumor as well as to establishment of metastases. Under normoxic conditions, CGRP is capable of stimulating cell replication and growth in cancer cells, demonstrating that it is relevant to the growth of a primary tumor. Under hypoxic conditions, CGRP is capable of stimulating cell replication and growth in a metastatic variant of a cancer cell line while it does not do so in a less metastatic variant. This demonstrates that CGRP signaling is relevant to the seeding and growth of metastatic, i.e., secondary, tumors.

Thus, the use of agents that modulate CGRP activity can be used to treat primary tumors as well as secondary tumors, where the tumor cells exist under normoxic or hypoxic conditions. Furthermore, for metastatic cancer cells that are in circulation and await implantation to form a secondary tumor, such agents can be used to prevent the implantation of those metastatic cells.

These methods are carried out through the use of an agent that modulates the activity of the CGRP receptor, including the prevention of CGRP from activating the receptor as well as agents that modify receptor function.

Figure 1:
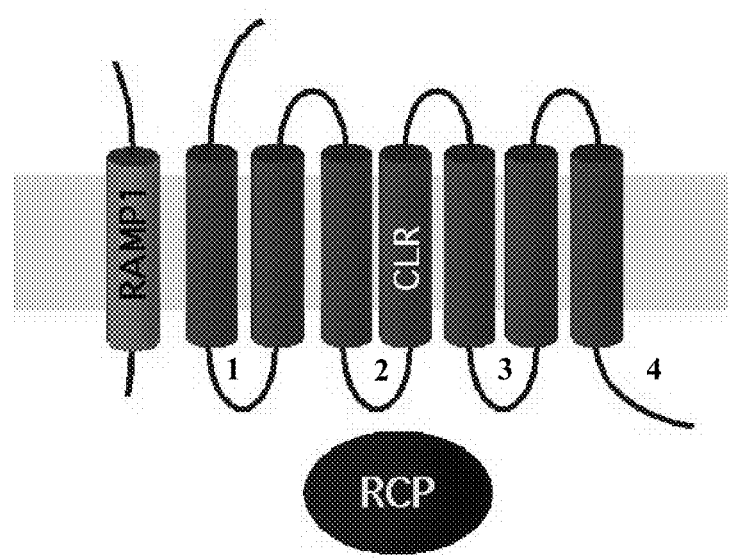
FIG. 1 is a model of the Calcitonin Gene-Related Peptide Receptor (CGRPC) showing the transmembrane components RAMP (Receptor Activity Modifying Protein) and CLR (Calcitonin-Like Receptor), as well as the intracellular protein RCP (CGRP-Receptor Component Protein).

The CGRP receptor, illustrated in FIG. 1, includes three components: calcitonin-like receptor ("CLR"), which is a G-protein coupled receptor; receptor activity modifying protein type 1 ("RAMP1"), which confers pharmacological specificity to the CGRP receptor; and the receptor component protein ("RCP"), which couples the CLR/RAMP1 complex to intracellular signaling pathways. Thus, agents that modulate the activity of the CGRP receptor can interfere with the interaction between any of these three components of the receptor, or between CGRP and the receptor.

Exemplary agents that modulate the CGRP receptor include, without limitation, a CGRP antagonist, a calcitonin-like receptor ("CLR") inhibitor, a receptor activity modifying protein 1 ("RAMP1") inhibitor, and a receptor component protein ("RCP") inhibitor. More specifically the CGRP receptor can be modulated using an antibody or fragment thereof or antibody mimic that binds specifically to CLR, an antibody or fragment thereof or antibody mimic that binds specifically to RAMP1, an antibody or fragment thereof or antibody mimic that binds specifically to RCP, an antibody or fragment thereof or antibody mimic that binds specifically to CGRP, a RAMP1 soluble protein or partial protein, a CLR soluble protein or partial protein, an antisense nucleic acid that disrupts expression of RAMP1, an antisense nucleic acid that disrupts expression of CLR, or an antisense nucleic acid that disrupts expression of RCP.

As used herein, the term "CGRP antagonist" means any agent that interferes with CGRP binding and/or activation of the CGRP receptor, including receptor signaling.

Exemplary CGRP antagonists include small molecule therapeutics that bind to CGRP, interfere with CGRP binding to its receptor, or block receptor activity. These include, without limitation, those described in PCT International Patent Application Nos. PCT/EP03/11762 to Rudolf et al., PCT/EP03/11763 to Rudolf et al., PCT/EP2004/000087 to Bauer et al., PCT/EP2005/003094 to Mueller et al., PCT/US03/16576 to Chaturvedula et al., PCT/US2004/040721 to Luo et al., PCT/US2003/038799 to Degnan et al., PCT/US2005/010330 to Degnan et al., PCT/GB99/03154 to Hill et al., PCT/US2004/007226 to Bell et al., PCT/US2004/007289 to Bell et al., PCT/US2004/007686 to Bell et al., PCT/US2004/007678 to Bell et al., PCT/US2004/007715 to Bell et al., PCT/US2004/011254 to Burgey et al., PCT/US2004/010851 to Burgey et al., PCT/US2004/011280 to Burgey et al., PCT/US2004/020206 to Burgey et al., PCT/US2004/021888 to Bell et al., PCT/US2004/020209 to Burgey et al., PCT/US2005/002199 to Burgey et al., PCT/US2005/031713 to Bell et al., PCT/US2005/031617 to Bell et al., PCT/US2005/031712 to Bell et al., PCT/US2005/032036 to Williams et al., PCT/US2005/032041 to Bell et al., PCT/US2005/032288 to Bell et al., PCT/US2005/035654 to Burgey et al., and U.S. Patent Application Publ. Nos. 20080139537 to Doods et al., 20080139591 to Doods et al., 20080125413 to Burgey et al. 20080113966 to Burgey et al., 20080096878 to Bell et al., 20080090806 to Paone et al., 20080070899 to Burgey et al., 20080004304 to Bell et al., 20080004261 to Gutierrez et al., 20070293470 to Williams et al., 20070287697 to Paone et al., 20070287696 to Burgey et al., 20070265225 to Wood et al., 2007/0259850 to Mercer et al., 20070225272 to Burgey et al., 20070149503 to Chaturvedula et al., 20070149502 to Chaturvedula et al., 20070111982 to Bell et al., 20070049577 to Han et al., 20060211712 to Bell et al., 20060194783 to Burgey et al., 20060189600 to Bell et al., 20060189593 to Bell et al., 20060183700 to Vater et al., 20060173046 to Bell et al., 20060148790 to Burgey et al., 20060148779 to Bell et al., 20060135511 to Burgey et al., 2006/0094707 to Chaturvedula et al., 20050256098 to Burgey et al., 20050215576 to Degnan et al., 20040229861 to Burgey et al., 20040204397 to Chaturvedula et al., and 20040063735 to Chaturvedula et al., each of which is hereby incorporated by reference in its entirety. Pharmaceutical compositions suitable for administering such agents are also disclosed therein.

There are presently three commercially available CGRP antagonists: BIBN4096BS (Boehringer Ingelheim), which is also known as olcegepant or N-((1R)-2-(((1S)-5-amino-1-((4-(pyridin-4-yl)piperazin-1-yl)carbonyl)pentyl)amino)-1-(3,5-dibromo-4-hydroxybenzyl)-2-oxoethyl)-4-(2-oxo-1,4-dihydroquinazolin-3(2H)-yl)piperidine-1-carboxamide (Edvinsson, "Clinical Data on the CGRP Antagonist BIBN4096Bs for Treatment of Migraine Attacks," *CNS Drug Rev.* 11(1):69-76 (2005), which is hereby incorporated by reference in its entirety); MK-0974 (Merck), which is also known as telcagepant or N-((3R,6S)-6-(2,3-Difluorophenyl)-2-oxo-1-(2,2,2-trifluoroethyl)hexahydro-1H-azepin-3-yl)-4-(2-oxo-2,3-dihydro-1H-imidazo[4,5-b]pyridin-1-yl)piperidine-1-carboxamide (Salvatore et al., "Pharmacological Characterization of MK-0974, a Potent and Orally Active CGRP Receptor Antagonist for the Treatment of Migraine," *J. Pharmacol. Exp. Ther.* 324(2):416-21 (2007), which is hereby incorporated by reference in its entirety); and MK-3207, which is also known as 2-((8R)-8-(3,5-Difluorophenyl)-10-oxo-6,9-diazaspiro(4.5)dec-9-yl)-N-((2R)-2'-oxo-1,1',2',3-tetrahydrospiro(indene-2,3'-pyrrolo[2,3-b]pyridin)-5-yl)acetamide (Bell et al., "Discovery of MK-3207: A Highly Potent, Orally Bioavailable CGRP Receptor Antagonist," *ACS Med. Chem. Lett.* 1(1):24-29 (2010); Salvatore et al., "Pharmacological Properties of MK-3207, a Potent and Orally Active Calcitonin Gene-related Peptide Receptor Antagonist," *J. Pharmacol. Exp. Ther.* 333(1):152-160 (2010), each of which is hereby incorporated by reference in its entirety). These drugs are or have been used in clinical trials for treatment of migraine.

A number of other CGRP antagonists are also known in the art. By way of example, suitable hydroxypyridine carboxamide CGRP antagonists include, without limitation, 4-bromo-N-(3,5-difluorobenzyl)-6-(1,1-dioxido-1,2-thiazinan-2-yl)-3-hydroxypyridine-2-carboxamide; 4-bromo-N-(3-fluorobenzyl)-6-(1,1-dioxido-1,2-thiazinan-2-yl)-3-hydroxypyridine-2-carboxamide; 4-bromo-N-(t-butyl-acetate)-6-(1,1-dioxido-1,2-thiazinan-2-yl)-3-hydroxypyridine-2-carboxamide; 4-bromo-N-((cyclobutylcarbamoyl)methyl)-6-(1,1-dioxido-1,2-thiazinan-2-yl)-3-hydroxypyridine-2-carboxamide; 4-bromo-N-((cyclohexylcarbamoyl)methyl)-6-(1,1-dioxido-1,2-thiazinan-2-yl)-3-hydroxypyridine-2-carboxamide; 4-bromo-N-((adamantylcarbamoyl)methyl)-6-(1,1-dioxido-1,2-thiazinan-2-yl)-3-hydroxypyridine-2-carboxamide; 4-bromo-N-((m-diphenylcarbamoyl)methyl)-6-(1,1-dioxido-1,2-thiazinan-2-yl)-3-hydroxypyridine-2-carboxamide; N-(3,5-difluorobenzyl)-6-(1,1-dioxido-1,2-thiazinan-2-yl)-8-hydroxynaphtyridine-7-carboxamide; N-(3-iodobenzyl)-6-(1,1-dioxido-1,2-thiazinan-2-yl)-8-hydroxynaphtyridine-7-carboxamide; N-(3,5-dichlorobenzyl)-6-(1,1-dioxido-1,2-thiazinan-2-yl)-8-hydroxynaphtyridine-7-carboxamide; methyl 2-{[3,5-difluorobenzyl)amino]carbonyl}-6-(1,1-dioxido-1,2-thiazinan-2-yl)-3-hydroxyisonicotinate; and methyl 2-({[t-butoxycarbonyl)methyl]amino}carbonyl)-6-(1,1-dioxido-1,2-thiazinan-2-yl)-3-hydroxyisonicotinate.

By way of example, suitable oxepino[3,4-e]indazol-8-one and azepino[3,4-e]indazol-8-one CGRP antagonists include, without limitation, (S)-4-bromo-7-(2-oxo-2-(4-(2-oxo-1,2-dihydroquinolin-3-yl)piperidin-1-yl)ethyl)-6,7-dihydro-3H-oxepino[3,4-e]indazol-8(10H)-one; (S)-1,4-dibromo-7-(2-oxo-2-(4-(2-oxo-1,2-dihydroquinolin-3-yl)piperidin-1-yl)ethyl)-9-(2,2,2-trifluoroethyl)-6,7,9,10-tetrahydroazepino[3,4-e]indazol-8(3H)-one; and (S)-1,4-dibromo-7-(2-(4-(8-fluoro-2-oxo-1,2-dihydroquinolin-3-yl)piperidin-1-yl)-2-oxoethyl)-9-(2,2,2-trifluoroethyl)-6,7,9,10-tetrahydroazepino[3,4-e]indazol-8(3H)-one.

By way of example, suitable azepine CGRP antagonists include, without limitation, N-[(3R,7R)-1-(cyclopropylmethyl)-2-oxo-7-phenylazepan-3-yl]-4-(2-oxo-1,4-dihydroquinazolin-3 (2H)-yl)piperidine-1-carboxamide; tert-butyl [(3R,7R)-2-oxo-3-({[4-(2-oxo-1,4-dihydroquinazolin-3 (2H)-yl)piperidin-1-yl]carbonyl}amino)-7-phenylazepan-1-yl acetate; tert-butyl [(3R,7R)-2-oxo-3-({[4-(2-oxo-1,2,4,5-tetrahydro-3H-1,3-benzodiazepin-3-yl)piperidin-1-yl]carbonyl}amino)-7-phenylazepan-1-yl]acetate; N-R (3R, 6S)-1-(cyclopropylmethyl)-2-oxo-6-phenylazepan-3-yl]-4-(2-oxo-1,4-dihydroquinazolin-3(2H)-yl) piperidine-1-carboxamide; N-R (3S,6R)-1-(cyclopropylmethyl)-2-oxo-6-phenylazepan-3-yl]-4-(2-oxo-1,4-dihydroquinazolin-3(2H)-yl) piperidine-1-carboxamide; cis-N-1-(cyclopropylmethyl)-2-oxo-6-phenylazepan-3-yl]-4-(2-oxo-1,4-dihydroquinazolin-3(2H)-yl) piperidine-1-carboxamide; N-R(3R,6S)-1-(cyclopropylmethyl)-2-oxo-6-phenylazepan-3-yll-4-(2-oxo-1,2,4,5-tetrahydro-3H-13-benzodiazepin-3-yl) piperidine-1-carboxamide; 4-(4-chloro-2-oxo-2,3-dihydro-1H-benzimidazol-1-yl)-N-f (3R,6S)-1-(2-methoxyethyl)-2-oxo-6-phenylazepan-3-yllpiperidine-1-carboxamide; N-f (3R,6S)-1-(2-methoxyethyl)-2-oxo-6-phenylazepan-3-yll-4-(4-methyl-2-oxo-2,3-dihydro-1H-benzimidazol-1-yl) piperidine-1-carboxamide; N-r (2S,6R)-4-(cyclopropylmethyl)-5-oxo-2-phenyl-14-oxazepan-6-yll-4-(2-oxo-1,2,4,5-tetrahydro-3H-1,3-benzodiazepin-3-yl) piperidine-1-carboxamide; N-(2S,6R)-4-(cyclopropylmethyl)-5-oxo-2-phenyl-1,4-oxazepan-6-yll-4-(2-oxo-2,3-dihydro-1H-benzimidazol-1-yl) piperidine-1-carboxamide; N-r (2S,6R)-4-(cyclopropylmethyl)-5-oxo-2-phenyl-1,4-oxazepan-6-yll-4-(6-fluoro-2-oxo-2,3-dihydro-1H-benzimidazol-1-yl) piperidine-1-carboxamide; N-f (2S*6R)-4-(cyclopropylmethyl)-5-oxo-2-phenyl-1,4-oxazepan-6-yll-4-(2-oxo-1,2-dihydroquinolin-3-yl) piperidine-1-carboxamide; N-r (2S, 6R and 2R,6S)-4-(cyclopropylmethyl)-5-oxo-2-phenyl-1,4-oxazepan-6-yll-4-(2-oxo-1,4-dihydroquinazolin-3(2H)-yl) piperidine-1-carboxamide; 19-(2R,6S and 2R,6R)-4-(cyclopropylmethyl)-5-oxo-2-phenyl-1,4-oxazepan-6-yll-4-(2-oxo-1,4-dihydroquinazolin-3(2H)-yl) piperidine-1-carboxamide; cis N-r (3S,6S and 3R,6R)-1-(cyclopropylmethyl)-7-oxo-3-phenyl-1,4-diazepan-6-yll-4-(2-oxo-1,4-dihydroquinazolin-3 (2H)-yl) piperidine-1-carboxamide; N-[(3R)-1-(cyclopropylmethyl)-2-oxoazepan-3-yll-4-(2-oxo-1,4-dihydroquinazolin-3 (2H)-yl) piperidine-1-carboxamide; N-r (3R)-1-benzyl-2-oxoazepan-3-yll-4-(2-oxo-1,4-dihydroquinazolin-3(2H)-yl) piperidine-1-carboxamide; N-(1-benzyl-2-oxoazepan-3-yl)-4-(2-oxo-1,2,4,5-tetrahydro-3H-1,3-benzodiazepin-3-yl) piperidine-1-carboxamide; N-f (3R)-1-(4-hydroxybenzyl)-2-oxoazepan-3-yll-4-(2-oxo-1,4-dihydroquinazolin-3(2H)-yl) piperidine-1-carboxamide; N-f (3R)-1-(3-methoxybenzyl)-2-oxoazepan-3-yll-4-(2-oxo-1,4-dihydroquinazolin-3(2H)-yl) piperidine-1-carboxamide; N-r (3R)-1-(3-Hydroxybenzyl)-2-oxoazepan-3-yll-4-(2-oxo-1 4-dihydroquinazolin-3(2H)-yl) piperidine-1-carboxamide; N-[1-benzyl-3-(4-hydroxybenzyl)-2-oxoazepan-3-yl]-4-(2-oxo-1,4-dihydroquinazolin-3(2H)-yl) piperidine-1-carboxamide; and N-[3-(4-methoxybenzyl)-2-oxoazepan-3-yll-4-(2-oxo-2,3-dihydro-1H-benzimidazol-1-yl) piperidine-1-carboxamide.

Peptide CGRP receptor antagonists are also disclosed in U.S. Patent Application Publ. No. 20020068814 to Smith et al., and U.S. Patent Application Publ. No. 20080020978 to Gegg et al., each of which is hereby incorporated by reference in its entirety. One exemplary peptide CGRP antagonist is $CGRP_{8-37}$, which consists of residues 8-37 of SEQ ID NO: 2 below (Chiba et al., "Calcitonin Gene-Related Peptide Receptor Antagonist Human CGRP(8-37)," *Am J Physiol* 256(2 Pt 1):E331-35 (1989), which is hereby incorporated by reference in its entirety).

Antibodies or fragments thereof, which specifically bind to any one of CGRP, CLR, RAMP1, RCP, or the CGRP receptor as a whole can also be used. The antibodies may be monoclonal or polyclonal, and can include active fragments thereof. The antibodies may be neutralizing antibodies in that they inhibit the activity of the protein(s) to which they bind. Also suitable are blocking antibodies that block the interaction between two proteins of the CGRP receptor thereby preventing CGRP receptor signaling.

Monoclonal antibody production may be effected by techniques which are well-known in the art (*Monoclonal Antibodies—Production, Engineering and Clinical Applications*, Ritter et al., Eds. Cambridge University Press, Cambridge, UK (1995), which is hereby incorporated by reference in its entirety). Basically, the process involves first obtaining immune cells (lymphocytes) from the spleen of a mammal (e.g., mouse) which has been previously immunized with the antigen of interest (i.e., CGRP, CLR, RAMP1, or RCP, or fragments thereof containing an epitope of interest) either in vivo or in vitro. The antibody-secreting lymphocytes are then fused with (mouse) myeloma cells or transformed cells, which are capable of replicating indefinitely in cell culture, thereby producing an immortal, immunoglobulin-secreting cell line. The resulting fused cells, or hybridomas, are cultured, and the resulting colonies screened for the production of the desired monoclonal antibodies. Colonies producing such antibodies are cloned, and grown either in vivo or in vitro to produce large quantities of antibody. A description of the theoretical basis and practical methodology of fusing such cells is set forth in Kohler and Milstein, "Continuous Culture of Fused Cell Secreting Antibody of Predefined Specificity," *Nature*, 256:495 (1975), which is hereby incorporated by reference in its entirety.

Mammalian lymphocytes are immunized by in vivo immunization of the animal (e.g., a mouse) with the protein or polypeptide of the present invention. Such immunizations are repeated as necessary at intervals of up to several weeks to obtain a sufficient titer of antibodies. Following the last antigen boost, the animals are sacrificed and spleen cells removed.

Fusion with mammalian myeloma cells or other fusion partners capable of replicating indefinitely in cell culture is effected by standard and well-known techniques, for example, by using polyethylene glycol (PEG) or other fusing agents. Milstein and Kohler, "Fusion Between Immunoglobin-Secreting and Nonsecreting Myeloma Cell Lines," *Eur. J. Immunol.*, 6:511 (1976), which is hereby incorporated by reference in its entirety. This immortal cell line, which is preferably murine, but may also be derived from cells of other mammalian species, including without limitation, rats and humans, is selected to be deficient in enzymes necessary for the utilization of certain nutrients, to be capable of rapid growth, and to have good fusion capability. Many such cell lines are known to those skilled in the art, and others are regularly described.

Procedures for raising polyclonal antibodies are also well known. Typically, such antibodies can be raised by administering the polypeptide containing the epitope of interest subcutaneously to New Zealand white rabbits which have first been bled to obtain pre-immune serum. The antigens can be injected at a total volume of 100 µl per site at six different sites. Each injected material will contain synthetic surfactant adjuvant pluronic polyols, or pulverized acrylamide gel containing the protein or polypeptide after SDS-polyacrylamide gel electrophoresis. The rabbits are then bled approximately every two weeks after the first injection and periodically boosted with the same antigen three times every six weeks. A sample of serum is then collected 10 days after each boost. Polyclonal antibodies are then recovered from the serum by affinity chromatography using the corresponding antigen to capture the antibody. This and other procedures for raising polyclonal antibodies are disclosed in Harlow et al., Eds., *Antibodies: A Laboratory Manual*, Cold Spring Harbor Laboratory, New York (1988), which is hereby incorporated by reference in its entirety. Mono-specific polyclonal antibodies can also be prepared by selecting those polyclonal antibodies that bind to a specific epitope, and antibodies that do not be are removed.

It is also possible to use the anti-idiotype technology to produce monoclonal antibodies that mimic an epitope. As used in this invention, "epitope" means any antigenic determinant on an antigen to which the paratope of an antibody binds. Epitopic determinants usually consist of chemically active surface groupings of molecules, such as amino acids or sugar side chains and usually have specific three dimensional structural characteristics, as well as specific charge characteristics. For example, an anti-idiotype monoclonal antibody made to a first monoclonal antibody will have a binding domain in the hypervariable region that is the image of the epitope bound by the first monoclonal antibody.

Also suitable for use in the present invention are antibody fragments engineered to bind to intracellular proteins, i.e., intrabodies. Particularly useful for carrying out the methods of the present invention are intrabodies directed to RCP or to the second cytoplasmic domain of the CLR that will prevent the RCP-CLR interaction, and thereby prevent CGRP receptor signaling. Intrabodies are generally obtained by selecting a single variable domain from variable regions of an antibody having two variable domains (i.e., a heterodimer of a heavy chain variable domain and a light chain variable domain). Single chain Fv fragments, Fab fragments, ScFv-Ck fusion proteins, single chain diabodies, $V_H$-$C_H$1 fragments, and even whole IgG molecules are suitable formats for intrabody development (Kontermann R. E., "Intrabodies as Therapeutic Agents," *Methods* 34:163-70 (2004), which is here by incorporated by reference in its entirety).

Intrabodies having antigen specificity for a CGRP receptor protein epitope can be obtained from phage display, yeast surface display, or ribosome surface display. Methods for producing libraries of intrabodies and isolating intrabodies of interest are further described in U.S. Published Patent Application No. 20030104402 to Zauderer and U.S. Published Patent Application No. 20050276800 to Rabbitts, which are hereby incorporated by reference in their entirety. Methods for improving the stability and affinity binding characteristics of intrabodies are described in WO2008070363 to Zhenping; Contreras-Martinez et al., "Intracellular Ribosome Display via SecM Translation Arrest as a Selection for Antibodies with Enhanced Cytosolic Stability," *J Mol Biol* 372(2):513-24 (2007), which are hereby incorporated by reference in their entirety.

In addition to whole antibodies, the present invention encompasses binding portions of such antibodies. Such binding portions include Fab fragments, Fab' fragments, F(ab)$_2$ fragments, F(ab')$_2$ fragments, Fd fragments, Fv fragments, dAb fragments, complementarity determining regions, single-chain antibodies (i.e., covalently linked variable heavy ($V_H$) and light ($V_L$) domains), single-domain antibodies (i.e., monomeric variable domains) (see, e.g., Holt et al., "Domain Antibodies: Proteins for Therapy," *Trends in Biotechnology* 21:484-490 (2003), which is hereby incorporated by reference in its entirety), and minibodies, e.g., 61-residue subdomains of the antibody heavy-chain variable domain (Pessi et al., "A Designed Metal-binding Protein with a Novel Fold," *Nature*, 362:367-369 (1993), which is hereby incorporated by reference in its entirety).

These antibody fragments can be made by conventional procedures, such as proteolytic fragmentation procedures, as described in J. Goding, *Monoclonal Antibodies: Principles and Practice*, (pp. 98-118) Academic Press: New York (1983), and Harlow et al., *Antibodies: A Laboratory Manual*, Cold Spring Harbor Laboratory, New York (1988), which are hereby incorporated by reference in their entirety, or other methods known in the art.

Exemplary CGRP neutralizing antibodies include those disclosed in PCT/US2006/062272 to Benschop et al., which is hereby incorporated by reference in its entirety. A number of antibodies directed against CGRP (Santa Cruz sc-8857, sc-28920, sc-8856, and sc-34588; Assay Designs (Enzo) anti-human CGRP monoclonal ABS 026-04-02), RAMP1 (Abnova H00010267-M01), CLR (Abnova H00010203-A01), and RCP (Santa Cruz sc-34588; Abnova H00027297-A01) are commercially available.

Additional antibodies can be raised using purified or recombinantly produced proteins as the antigen in the procedures described above. Purified proteins can be obtained using via recombinant expression followed by standard purification procedures.

CGRP is a 37 amino acid peptide that is derived from the calcitonin-related polypeptide alpha (Genbank Accession Nos. NM_001033952 and NM_001033953, each of which is hereby incorporated by reference in its entirety). An exemplary nucleotide sequence encoding the CGRP is shown below as SEQ ID NO:1:

```
gcctgtgaca ctgccacctg tgtgactcat cggctggcgg gcttgctgag cagatcaggg    60
ggtgtggtga agaacaactt tgtgcccacc aatgtgggtt ccaaagcctt c            111
```

Additional nucleotide sequences encoding the CGRP peptide are described in U.S. Pat. No. 4,736,023 to Evan et al., which is hereby incorporated by reference in its entirety.

The amino acid sequence of CGRP is shown as SEQ ID NO:2 below:

```
Ala Cys Asp Thr Ala Thr Cys Val Thr His Arg Leu Ala Gly Leu Leu
1               5                   10                  15

Ser Arg Ser Gly Gly Val Val Lys Asn Asn Phe Val Pro Thr Asn Val
            20                  25                  30

Gly Ser Lys Ala Phe
            35
```

Additional details concerning CGRP are disclosed at Genbank Accession 1005250A, which is hereby incorporated by reference in its entirety. Homologous CGRP amino acid sequences that are known in the art and can be used to carry out the methods of the present invention include a CGRP amino acid sequence having at least about 65 percent or 70 percent identity to SEQ ID NO: 2, more preferably at least about 75 percent or 80 percent identity to SEQ ID NO: 2, most preferably at least about 85 percent or 90 percent identity to SEQ ID NO: 2. Homologs having at least about 95 percent identity to SEQ ID NO: 2 are even more preferred.

Exemplary homologs of SEQ ID NO: 2 include, without limitation, the human calcitonin-related polypeptide beta, Genbank Accession NP-000719, having 91% sequence identity to the CGRP peptide derived from the human calcitonin-related polypeptide alpha; rat (*Rattus norvegicus*) CGRP alpha, Genbank Accession AAU07931, having 89% sequence identity to the human CGRP sequence; mouse (*Mus musculus*) CGRP alpha, Genbank Accession AAK06841, having 89% sequence identity to the human CGRP sequence; sheep (*Ovis aries*) CGRP alpha, Genbank Accession AAB23468, having 89% identity to the human CGRP sequence; and dog (*Canis familiaris*) CGRP alpha, Genbank Accession CAB97487, having 91% identity to the human CGRP sequence. Each of the above referenced Genbank Accession entries and corresponding sequences are hereby incorporated by reference in their entirety.

An exemplary human RAMP1 nucleotide sequence is shown below (SEQ ID NO:3):

```
atggcccggg ccctgtgccg cctcccgcgg cgcggcctct ggctgctcct ggcccatcac    60
ctcttcatga ccactgcctg ccaggaggct aactacggtg ccctcctccg ggagctctgc   120
ctcacccagt tccaggtaga catggaggcc gtcggggaga cgctgtggtg tgactggggc   180
aggaccatca ggagctacag ggagctggcc gactgcacct ggcacatggc ggagaagctg   240
ggctgcttct ggcccaatgc agaggtggac aggttcttcc tggcagtgca tggccgctac   300
ttcaggagct gccccatctc aggcagggcc gtgcgggacc cgcccggcag catcctctac   360
cccttcatcg tggtccccat cacggtgacc ctgctggtga cggcactggt ggtctggcag   420
agcaagcgca ctgagggcat tgtgtag                                      447
```

This nucleotide sequence encodes the following RAMP1 protein (SEQ ID NO:4).

```
Met Ala Arg Ala Leu Cys Arg Leu Pro Arg Arg Gly Leu Trp Leu Leu
1               5                   10                  15

Leu Ala His His Leu Phe Met Thr Thr Ala Cys Gln Glu Ala Asn Tyr
                20                  25                  30

Gly Ala Leu Leu Arg Glu Leu Cys Leu Thr Gln Phe Gln Val Asp Met
                35                  40                  45

Glu Ala Val Gly Glu Thr Leu Trp Cys Asp Trp Gly Arg Thr Ile Arg
        50                  55                  60

Ser Tyr Arg Glu Leu Ala Asp Cys Thr Trp His Met Ala Glu Lys Leu
65                  70                  75                  80

Gly Cys Phe Trp Pro Asn Ala Glu Val Asp Arg Phe Phe Leu Ala Val
                85                  90                  95

His Gly Arg Tyr Phe Arg Ser Cys Pro Ile Ser Gly Arg Ala Val Arg
                100                 105                 110

Asp Pro Pro Gly Ser Ile Leu Tyr Pro Phe Ile Val Val Pro Ile Thr
                115                 120                 125

Val Thr Leu Leu Val Thr Ala Leu Val Val Trp Gln Ser Lys Arg Thr
                130                 135                 140

Glu Gly Ile Val
145
```

Additional details concerning RAMP1 are disclosed at Genbank Accession NM_005855, which is hereby incorporated by reference in its entirety. Homologous RAMP1 amino acid sequences that are known in the art and can be used to carry out the methods of the present invention include RAMP1 amino acid sequences having at least about 65 percent or 70 percent identity to SEQ ID NO: 4, more preferably at least about 75 percent or 80 percent identity to SEQ ID NO: 4, most preferably at least about 85 percent or 90 percent identity to SEQ ID NO: 4. Homologs having at least about 95 percent identity to SEQ ID NO: 4 are even more preferred.

Exemplary homologs of SEQ ID NO: 4 include, without limitation, chimpanzee (*Pan troglodytes*) RAMP1, Genbank Accession XP 516183, having 97% sequence identity to the human RAMP1 sequence; rat (*Rattus norvegicus*) RAMP1, Genbank Accession NP_113833, having 71% sequence identity to the human RAMP1 sequence; mouse (*Mus musculus*) RAMP1, Genbank Accession NP_058590, having 70% sequence identity to the human RAMP1 sequence; and guinea pig (*Cavia Porcellus*) RAMP1, Genbank Accession Q8R4C6, having 71% sequence identity to the human RAMP1 sequence. Each of the above referenced Genbank Accession entries and corresponding sequences are hereby incorporated by reference in their entirety.

An exemplary human CLR nucleotide sequence is shown below (SEQ ID NO: 5).

```
atggagaaaa agtgtaccct gtattttctg gttctcttgc ctttttttat gattcttgtt      60
acagcagaat tagaagagag tcctgaggac tcaattcagt ggggagttac tagaaataaa     120
atcatgacag ctcaatatga atgttaccaa aagattatgc aagacccat tcaacaagca      180
gaaggcgttt actgcaacag aacctgggat ggatggctct gctggaacga tgttgcagca     240
ggaactgaat caatgcagct ctgccctgat tactttcagg actttgatcc atcagaaaaa     300
gttacaaaga tctgtgacca agatggaaac tggtttagac atccagcaag caacagaaca     360
tggacaaatt atacccagtg taatgttaac acccacgaga aagtgaagac tgcactaaat     420
ttgttttacc tgaccataat tggacacgga ttgtctattg catcactgct tatctcgctt     480
ggcatattct tttatttcaa gagcctaagt tgccaaagga ttaccttaca caaaaatctg     540
ttcttctcat ttgtttgtaa ctctgttgta acaatcattc acctcactgc agtggccaac     600
aaccaggcct tagtagccac aaatcctgtt agttgcaaag tgtcccagtt cattcatctt     660
tacctgatgg gctgtaatta cttttggatg ctctgtgaag gcatttacct acacacactc     720
attgtggtgg ccgtgtttgc agagaagcaa catttaatgt ggtattattt tcttggctgg     780
ggatttccac tgattcctgc ttgtatacat gccattgcta gaagcttata ttacaatgac     840
aattgctgga tcagttctga tacccatctc ctctacatta tccatggccc aatttgtgct     900
gctttactgg tgaatctttt tttcttgtta aatattgtac gcgttctcat caccaagtta     960
aaagttacac accaagcgga atccaatctg tacatgaaag ctgtgagagc tactcttatc    1020
ttggtgccat tgcttggcat tgaatttgtg ctgattccat ggcgacctga aggaaagatt    1080
gcagaggagg tatatgacta catcatgcac atccttatgc acttccaggg tcttttggtc    1140
tctaccattt tctgcttctt taatggagag gttcaagcaa ttctgagaag aaactggaat    1200
caatacaaaa tccaatttgg aaacagcttt tccaactcag aagctcttcg tagtgcgtct    1260
tacacagtgt caacaatcag tgatggtcca ggttatagtc atgactgtcc tagtgaacac    1320
ttaaatggaa aaagcatcca tgatattgaa aatgttctct aaaaccaga aaatttatat    1380
aattga                                                               1386
```

This nucleotide sequence encodes the following CLR protein (SEQ ID NO:6).

```
Met Glu Lys Lys Cys Thr Leu Tyr Phe Leu Val Leu Leu Pro Phe Phe
1               5                   10                  15

Met Ile Leu Val Thr Ala Glu Leu Glu Glu Ser Pro Glu Asp Ser Ile
                20                  25                  30

Gln Leu Gly Val Thr Arg Asn Lys Ile Met Thr Ala Gln Tyr Glu Cys
            35                  40                  45
```

-continued

```
Tyr Gln Lys Ile Met Gln Asp Pro Ile Gln Gln Ala Glu Gly Val Tyr
 50                  55                  60
Cys Asn Arg Thr Trp Asp Gly Trp Leu Cys Trp Asn Asp Val Ala Ala
 65                  70                  75                  80
Gly Thr Glu Ser Met Gln Leu Cys Pro Asp Tyr Phe Gln Asp Phe Asp
                 85                  90                  95
Pro Ser Glu Lys Val Thr Lys Ile Cys Asp Gln Asp Gly Asn Trp Phe
                100                 105                 110
Arg His Pro Ala Ser Asn Arg Thr Trp Thr Asn Tyr Thr Gln Cys Asn
            115                 120                 125
Val Asn Thr His Glu Lys Val Lys Thr Ala Leu Asn Leu Phe Tyr Leu
130                 135                 140
Thr Ile Ile Gly His Gly Leu Ser Ile Ala Ser Leu Leu Ile Ser Leu
145                 150                 155                 160
Gly Ile Phe Phe Tyr Phe Lys Ser Leu Ser Cys Gln Arg Ile Thr Leu
                165                 170                 175
His Lys Asn Leu Phe Phe Ser Phe Val Cys Asn Ser Val Val Thr Ile
            180                 185                 190
Ile His Leu Thr Ala Val Ala Asn Asn Gln Ala Leu Val Ala Thr Asn
        195                 200                 205
Pro Val Ser Cys Lys Val Ser Gln Phe Ile His Leu Tyr Leu Met Gly
        210                 215                 220
Cys Asn Tyr Phe Trp Met Leu Cys Glu Gly Ile Tyr Leu His Thr Leu
225                 230                 235                 240
Ile Val Val Ala Val Phe Ala Glu Lys Gln His Leu Met Trp Tyr Tyr
                245                 250                 255
Phe Leu Gly Trp Gly Phe Pro Leu Ile Pro Ala Cys Ile His Ala Ile
                260                 265                 270
Ala Arg Ser Leu Tyr Tyr Asn Asp Asn Cys Trp Ile Ser Ser Asp Thr
            275                 280                 285
His Leu Leu Tyr Ile Ile His Gly Pro Ile Cys Ala Ala Leu Leu Val
        290                 295                 300
Asn Leu Phe Phe Leu Leu Asn Ile Val Arg Val Leu Ile Thr Lys Leu
305                 310                 315                 320
Lys Val Thr His Gln Ala Glu Ser Asn Leu Tyr Met Lys Ala Val Arg
                325                 330                 335
Ala Thr Leu Ile Leu Val Pro Leu Leu Gly Ile Glu Phe Val Leu Ile
            340                 345                 350
Pro Trp Arg Pro Glu Gly Lys Ile Ala Glu Glu Val Tyr Asp Tyr Ile
            355                 360                 365
Met His Ile Leu Met His Phe Gln Gly Leu Leu Val Ser Thr Ile Phe
        370                 375                 380
Cys Phe Phe Asn Gly Glu Val Gln Ala Ile Leu Arg Arg Asn Trp Asn
385                 390                 395                 400
Gln Tyr Lys Ile Gln Phe Gly Asn Ser Phe Ser Asn Ser Glu Ala Leu
                405                 410                 415
Arg Ser Ala Ser Tyr Thr Val Ser Thr Ile Ser Asp Gly Pro Gly Tyr
            420                 425                 430
Ser His Asp Cys Pro Ser Glu His Leu Asn Gly Lys Ser Ile His Asp
        435                 440                 445
Ile Glu Asn Val Leu Leu Lys Pro Glu Asn Leu Tyr Asn
450                 455                 460
```

Additional details concerning CLR are disclosed at Genbank Accession NM_005795, which is hereby incorporated by reference in its entirety. Homologous CLR amino acid sequences that are known in the art and can be used to carry out the methods of the present invention include CLR amino acid sequences having at least about 65 percent or 70 percent identity to SEQ ID NO: 6, more preferably at least about 75 percent or 80 percent identity to SEQ ID NO: 6, most preferably at least about 85 percent or 90 percent identity to SEQ ID NO: 6. Homologs having at least about 95 percent identity to SEQ ID NO: 6 are even more preferred.

Exemplary homologs of SEQ ID NO: 6 include, without limitation, orangutan (*Pongo abelii*) CLR, Genbank Accession NP_001125204, having 100% sequence identity to the human CLR sequence; chimpanzee (*Pan troglodytes*) CLR, Genbank Accession XP_001161496, having 96% sequence identity to the human CLR sequence; horse (*Equus caballus*) CLR, Genbank Accession XP_001501718, having 93% sequence identity to the human CLR sequence; dog (*Canis familiaris*) CLR, Genbank Accession XP_545560, having 93% sequence identity to the human CLR sequence; mouse (*Mus musculus*) CLR, Genbank Accession NP_061252, having 90% sequence identity to the human CLR sequence; and rat (*Rattus norvegicus*) CLR, Genbank Accession NP_036849, having 90% sequence identity to the human CLR sequence. Each of the above referenced Genbank Accession entries and corresponding sequences are hereby incorporated by reference in their entirety.

An exemplary human RCP (also known as RCP9) nucleotide sequence is shown below (SEQ ID NO:7):

```
atggaagtga aggatgccaa ttctgcgctt ctcagtaact acgaggtatt tcagttacta    60
actgatctga aagagcagcg taaagaaagt ggaaagaata aacacagctc tgggcaacag   120
aacttgaaca ctatcaccta tgaaacgtta aaatacatat caaaaacacc atgcaggcac   180
cagagtcctg aaattgtcag agaatttctc acagcattga aaagccacaa gttgaccaaa   240
gctgagaagc tccagctgct gaaccaccgg cctgtgactg ctgtggagat ccagctgatg   300
gtggaagaga gtgaagagcg gctcacggag gagcagattg aagctcttct ccacaccgtc   360
accagcattc tgcctgcaga gccagaggct gagcagaaga agaatacaaa cagcaatgtg   420
gcaatggacg aagaggaccc agcatag                                        447
```

This nucleotide sequence encodes the following RCP protein (SEQ ID NO:8).

```
Met Glu Val Lys Asp Ala Asn Ser Ala Leu Leu Ser Asn Tyr Glu Val
1               5                   10                  15

Phe Gln Leu Leu Thr Asp Leu Lys Glu Gln Arg Lys Glu Ser Gly Lys
            20                  25                  30

Asn Lys His Ser Ser Gly Gln Gln Asn Leu Asn Thr Ile Thr Tyr Glu
            35                  40                  45

Thr Leu Lys Tyr Ile Ser Lys Thr Pro Cys Arg His Gln Ser Pro Glu
        50                  55                  60

Ile Val Arg Glu Phe Leu Thr Ala Leu Lys Ser His Lys Leu Thr Lys
65                  70                  75                  80

Ala Glu Lys Leu Gln Leu Leu Asn His Arg Pro Val Thr Ala Val Glu
            85                  90                  95

Ile Gln Leu Met Val Glu Glu Ser Glu Glu Arg Leu Thr Glu Glu Gln
            100                 105                 110

Ile Glu Ala Leu Leu His Thr Val Thr Ser Ile Leu Pro Ala Glu Pro
            115                 120                 125

Glu Ala Glu Gln Lys Lys Asn Thr Asn Ser Asn Val Ala Met Asp Glu
            130                 135                 140

Glu Asp Pro Ala
145
```

Additional details concerning RCP are disclosed at Genbank Accession AK311829, which is hereby incorporated by reference in its entirety. Homologous RCP amino acid sequences that are known in the art and can be used to carry out the methods of the present invention include RCP amino acid sequences having at least about 65 percent or 70 percent identity to SEQ ID NO: 8, more preferably at least about 75 percent or 80 percent identity to SEQ ID NO: 8, most preferably at least about 85 percent or 90 percent identity to SEQ ID NO: 8. Homologs having at least about 95 percent identity to SEQ ID NO: 8 are even more preferred.

Exemplary homologs of SEQ ID NO: 8 include, without limitation, cattle (*Bos taurus*) RCP, Genbank Accession NP_001071338, having 90-93% sequence identity to the human RCP sequence; horse (*Equus caballus*) RCP, Genbank Accession XP_001493592, having 93% sequence identity to the human RCP sequence; dog (*Canis familiaris*) RCP, Genbank Accession XP_536833, having 93% sequence identity to the human RCP sequence; mouse (*Mus musculus*) RCP, Genbank Accession NP_031787, having 88% sequence identity to the human RCP sequence; guinea pig (*Cavia porcellus*) RCP, Genbank Accession Q60482, having 83% sequence identity to the human RCP sequence; and rat (*Rattus norvegicus*) RCP, Genbank Accession NP 446122, having 87% sequence identity to the human RCP sequence. Each of the above referenced Genbank Accession entries and corresponding sequences are hereby incorporated by reference in their entirety.

The recombinant expression of these and other proteins or polypeptides generally involves inserting a DNA molecule of interest (encoding the full length protein or, for example, and extracellular fragment thereof) into an expression system to which the DNA molecule is heterologous, i.e., not normally present. The heterologous DNA molecule is inserted into the expression system or vector in sense orientation and correct reading frame relative to regulatory sequences for the transcription and translation of the inserted protein-coding sequences.

With respect to the recombinant expression systems, an expression vector containing a DNA molecule encoding the recombinant protein or polypeptide can be made using common techniques in the art. The nucleic acid molecules, including those identified above or portions thereof, can be inserted into any of the many available expression vectors using reagents that are well known in the art. In preparing a DNA vector for expression, the various DNA sequences may normally be inserted or substituted into a bacterial plasmid. Any convenient plasmid may be employed, which will be characterized by having a bacterial replication system, a marker which allows for selection in a bacterium, and generally one or more unique, conveniently located restriction sites. The selection of a vector will depend on the preferred transformation technique and target host for transformation. The DNA can also be transferred to other vectors that are specific for use with other systems.

A variety of host-vector systems may be utilized to express the recombinant proteins or polypeptides. Primarily, the vector system must be compatible with the host cell used. Host-vector systems include but are not limited to the following: bacteria transformed with bacteriophage DNA, plasmid DNA, or cosmid DNA; microorganisms such as yeast containing yeast vectors; mammalian cell systems infected with virus (e.g., vaccinia virus, adenovirus, adeno-associated virus, etc.); insect cell systems infected with virus (e.g., baculovirus); and plant cells infected by bacteria (e.g., *Agrobacterium*). The expression elements of these vectors vary in their strength and specificities. Depending upon the host-vector system utilized, any one of a number of suitable transcription and translation elements can be used.

When recombinantly produced, the protein or polypeptide is expressed in a recombinant host cell, which can be either a prokaryote or a eukaryote.

Suitable vectors for practicing the present invention include, but are not limited to, the following viral vectors such as lambda vector system gt11, gtWES.tB, Charon 4, and plasmid vectors such as pCMV, pBR322, pBR325, pACYC177, pACYC184, pUC8, pUC9, pUC18, pUC19, pLG339, pR290, pKC37, pKC101, SV 40, pBluescript II SK+/− or KS+/− (see "Stratagene Cloning Systems" Catalog (1993)), pQE, pIH821, pGEX, pET series (Studier et al, "Use of T7 RNA Polymerase to Direct Expression of Cloned Genes," *Methods in Enzymology* 185:60-89 (1990), which is hereby incorporated by reference in its entirety), and any derivatives thereof. Any appropriate vectors now known or later described for genetic transformation are suitable for use with the present invention.

The DNA sequences can cloned into the vector using standard cloning procedures in the art, as described by Maniatis et al., *Molecular Cloning: A Laboratory Manual*, Cold Springs Harbor, N.Y.: Cold Springs Laboratory, (1982), which is hereby incorporated by reference in its entirety. U.S. Pat. No. 4,237,224 issued to Cohen and Boyer, which is hereby incorporated by reference in its entirety, describes the production of expression systems in the form of recombinant plasmids using restriction enzyme cleavage and ligation with DNA ligase. These recombinant plasmids are then introduced by means of transformation and replicated in unicellular cultures including prokaryotic organisms and eukaryotic cells grown in tissue culture.

Different genetic signals and processing events control many levels of gene expression (e.g., DNA transcription and messenger RNA (mRNA) translation).

Transcription of DNA is dependent upon the presence of a promoter, which is a DNA sequence that directs the binding of RNA polymerase and thereby promotes mRNA synthesis. The DNA sequences of eukaryotic promoters differ from those of prokaryotic promoters. Furthermore, eukaryotic promoters and accompanying genetic signals may not be recognized in or may not function in a prokaryotic system, and, further, prokaryotic promoters are not recognized and do not function in eukaryotic cells.

The promoter used for expression of the above-identified proteins or polypeptide fragments thereof can be a constitutive promoter, which directs expression continually, or an inducible promoter, which is capable of directly or indirectly activating transcription of one or more DNA sequences or genes in response to an inducer (whereas, in the absence of an inducer the DNA sequences or genes will not be transcribed). In addition, any enhancer or inducer elements can be included to generate the level and control over expression of the transgene.

The DNA construct of the present invention can also include an operable 3' regulatory region, selected from among those which are capable of providing correct transcription termination and polyadenylation of mRNA for expression in the host cell of choice, operably linked to a DNA molecule which encodes for a protein of choice.

The vector of choice, promoter, and an appropriate 3' regulatory region can be ligated together to produce the DNA construct of the present invention using well known molecular cloning techniques as described in Sambrook et al., *Molecular Cloning: A Laboratory Manual*, Second Edition, Cold Spring Harbor Press, NY (1989), and Ausubel, F. M. et al. *Current Protocols in Molecular Biology*, New York, N.Y.: John Wiley & Sons (1989), which are hereby incorporated by reference in their entirety.

As noted, one alternative to the use of prokaryotic host cells is the use of eukaryotic host cells, such as mammalian cells, which can also be used to recombinantly produce the various proteins or polypeptide fragments thereof as noted above. Mammalian cells suitable for carrying out the present invention include, among others: COS (e.g., ATCC No. CRL 1650 or 1651), BHK (e.g., ATCC No. CRL 6281), CHO (ATCC No. CCL 61), HeLa (e.g., ATCC No. CCL 2), 293 (ATCC No. 1573), CHOP, NS-1, NIH3T3 (ATCC No. CRL 1658), CNS1, and MDA-MB-231 (ATCC No. HTB-26) cells. Suitable expression vectors for directing expression in mammalian cells generally include a promoter, as well as other transcription and translation control sequences known in the art. Common promoters include SV40, MMTV, metallothionein-1, adenovirus E1a, CMV, immediate early, immunoglobulin heavy chain promoter and enhancer, and RSV-LTR.

Once the DNA construct of the present invention has been prepared, it is ready to be incorporated into a host cell. Recombinant molecules can be introduced into cells via transformation, particularly transfection, lipofection, transduction, conjugation, mobilization, electroporation, or infection (e.g., with a viral vector). Accordingly, another aspect of the present invention relates to a method of making a recombinant host cell. Basically, this method is carried out by transforming a host cell with a DNA construct of the present invention under conditions effective to yield transcription of the DNA molecule in the host cell.

Once the host cell has been prepared, the protein or polypeptide fragment can be expressed and recovered in a substantially pure form. In a particular embodiment, the substantially pure protein or polypeptide is at least about 80% pure, more preferably at least 90% pure, most preferably at least 95% pure. A substantially protein or polypeptide fragment can be obtained by conventional techniques well known in the art. Typically, the substantially pure protein or polypeptide is secreted into the growth medium of recombinant host cells. Alternatively, the substantially pure protein or polypeptide is produced but not secreted into growth medium. In such cases, to isolate the substantially pure protein or polypeptide, the host cell carrying a recombinant plasmid is propagated, lysed by sonication, heat, or chemical treatment, and then the homogenate is centrifuged to remove cell debris. The supernatant is then subjected to sequential ammonium sulfate precipitation. The fraction containing the substantially pure protein or polypeptide is subjected to gel filtration in an appropriately sized dextran or polyacrylamide column to separate the protein or polypeptide. If necessary, a protein fraction (containing the substantially pure CGRP, RAMP1, CLR or RCP protein or polypeptide) may be further purified by high performance liquid chromatography ("HPLC").

The CGRP antagonist can also be a soluble or partial protein of one or more of the CGRP receptor proteins. In particular, the soluble or partial protein is preferably a polypeptide fragment of either the RAMP1 protein, the RCP protein, or the CLR protein. Soluble or partial proteins of RAMP1, RCP, or CLR can be prepared using standard recombinant technology followed by standard protein purification procedures, both of which are described above. The soluble or partial protein can include fragments thereof lacking in cell membrane domains. The cell membrane domains of these proteins are known in the art (Conner, et al., "A Key Role for Transmembrane Prolines in Calcitonin Receptor-like Receptor Agonist Binding and Signalling: Implications for Family B G-Protein-coupled Receptors," *Mol. Pharmacol.* 67:20-31 (2005), which is hereby incorporated by reference in its entirety), and therefore soluble or partial polypeptides thereof can be produced by using DNA fragments that encode the desired fragment of the RAMP1, RCP, or CLR proteins. One suitable fragment is the second cytoplasmic loop of the CLR. These fragments can be introduced into expression vectors and then host cells in the manner described above.

The CGRP antagonist can also be an antibody mimic, a number of which are known in the art including, without limitation, those known as monobodies and those known as affibodies. Monobodies are derived from the tenth human fibronectin type III domain ($^0$Fn3) (Koide et al., "The Fibronectin Type III Domain as a Scaffold for Novel Binding Proteins," *J. Mol. Biol.* 284:1141-1151 (1998); Koide et al., "Probing Protein Conformational Changes in Living Cells by Using Designer Binding Proteins: Application to the Estrogen Receptor," *Proc. Natl. Acad. Sci. USA* 99:1253-1258 (2002), each of which is hereby incorporated by reference in its entirety). Affibodies are derived from the stable alpha-helical bacterial receptor domain Z of staphylococcal protein A (Nord et al., "Binding Proteins Selected from Combinatorial Libraries of an alpha-helical Bacterial Receptor Domain," *Nature Biotechnol.* 15(8):772-777 (1997), which is hereby incorporated by reference in its entirety). Variations in the antibody mimics can be created by substituting one or more domains of these polypeptides and then screening the modified monobodies or affibodies for selective binding activity (i.e., against one or more of CLR, RAMP1, and RCP).

According to another embodiment, the CGRP antagonist is a nucleic acid molecule known as an aptamer. Aptamers are single-stranded, partially single-stranded, partially double-stranded, or double-stranded nucleotide sequences, advantageously a replicatable nucleotide sequence, capable of specifically recognizing a selected non-oligonucleotide molecule or group of molecules (in this case, one or more of CLR, RAMP1, and RCP) by a mechanism other than Watson-Crick base pairing or triplex formation. Aptamers include, without limitation, defined sequence segments and sequences comprising nucleotides, ribonucleotides, deoxyribonucleotides, nucleotide analogs, modified nucleotides and nucleotides comprising backbone modifications, branchpoints and non-nucleotide residues, groups or bridges. Aptamers include partially and fully single-stranded and double-stranded nucleotide molecules and sequences; synthetic RNA, DNA, and chimeric nucleotides; hybrids; duplexes; heteroduplexes; and any ribonucleotide, deoxyribonucleotide, or chimeric counterpart thereof and/or corresponding complementary sequence, promoter, or primer-annealing sequence needed to amplify, transcribe, or replicate all or part of the aptamer molecule or sequence.

Nucleic acid aptamers include multivalent aptamers and bivalent aptamers. Methods of making bivalent and multivalent aptamers and their expression in multi-cellular organisms are described in U.S. Pat. No. 6,458,559 to Shi et al., which is hereby incorporated by reference in its entirety. A method for modular design and construction of multivalent nucleic acid aptamers, their expression, and methods of use are described in U.S. Patent Publication No. 2005/0282190, which is hereby incorporated by reference in its entirety. Aptamers may be designed to antagonize CGRP activity, disrupt the CGRP receptor, or disrupt CGRP binding to its receptor.

Identifying suitable nucleic acid aptamers of the present invention that antagonize CGRP basically involves selecting aptamers that bind CGRP or one or more of CLR, RAMP1, and RCP with sufficiently high affinity (e.g., $K_d$=20-50 nM) and specificity from a pool of nucleic acids containing a random region of varying or predetermined length (see Shi et al., "A Specific RNA Hairpin Loop Structure Binds the RNA Recognition Motifs of the *Drosophila* SR Protein B52," *Mol. Cell. Biol.* 17:1649-1657 (1997); Shi, "Perturbing Protein Function with RNA Aptamers" (thesis, Cornell University) microformed on (University Microfilms, Inc. 1997), which are hereby incorporated by reference in their entirety).

Identifying suitable nucleic acid aptamers can be carried out using an established in vitro selection and amplification scheme known as SELEX. The SELEX scheme is described in detail in U.S. Pat. No. 5,270,163 to Gold et al.; Ellington and Szostak, "In Vitro Selection of RNA Molecules that Bind Specific Ligands," *Nature* 346:818-822 (1990); and Tuerk & Gold, "Systematic Evolution of Ligands by Exponential Enrichment: RNA Ligands to Bacteriophage T4 DNA Polymerase," *Science* 249:505-510 (1990), which are hereby incorporated by reference in their entirety. The SELEX procedure can be modified so that an entire pool of aptamers with binding affinity can be identified by selectively partitioning the pool of aptamers. This procedure is described in U.S. Patent Application Publication No. 2004/0053310 to Shi et al., which is hereby incorporated by reference in its entirety.

Aptamers that bind to and inhibit activity of CGRP, or one or more of CLR, RAMP1, and RCP, may be identified using screening assays such as yeast-two hybrid approaches described in U.S. Patent Application Serial No. 20040210040 to Landolfi et al., which is hereby incorporated by reference in its entirety.

Alternatively, the CGRP receptor can be effectively blocked in the cancer cells by using an antisense nucleic acid construct that disrupts expression of one or more of RAMP1, CLR, or RCP. Given its specificity for CGRP, RAMP1 disruption is particularly preferred.

A number of suitable antisense techniques can be employed, including full length antisense constructions, e.g., using the RAMP1 nucleotide sequence identified above, which is insert in reverse orientation relative to a promoter to form an antisense construct that expresses a full length antisense RAMP1 mRNA.

Alternatively, any of a number of interfering RNA (RNAi) processes can also be employed. Numerous reports have been published on critical advances in the understanding of the biochemistry and genetics of both gene silencing and RNAi (Matzke et al., "RNA-Based Silencing Strategies in Plants," *Curr. Opin. Genet. Dev.* 11(2):221-227 (2001), which is hereby incorporated by reference in its entirety). In RNAi, the introduction of double stranded RNA (dsRNA, or iRNA, for interfering RNA) into animal or plant cells leads to the destruction of the endogenous, homologous mRNA, phenocopying a null mutant for that specific gene. In both post-transcriptional gene silencing and RNAi, the dsRNA is processed to short interfering molecules of 21-, 22-, or 23-nucleotide RNAs (siRNA) by a putative RNAaseIII-like enzyme (Tuschl T., "RNA Interference and Small Interfering RNAs," *Chembiochem* 2:239-245 (2001); Zamore et al., "RNAi: Double Stranded RNA Directs the ATP-Dependent Cleavage of mRNA at 21 to 23 Nucleotide Intervals," *Cell* 101:25-3, (2000), each of which is hereby incorporated by reference in its entirety). The endogenously generated siR-NAs mediate and direct the specific degradation of the target mRNA. In the case of RNAi, the cleavage site in the mRNA molecule targeted for degradation is located near the center of the region covered by the siRNA (Elbashir et al., "RNA Interference is Mediated by 21- and 22-Nucleotide RNAs," *Gene Dev.* 15(2):188-200 (2001), which is hereby incorporated by reference in its entirety).

The dsRNA for RAMP1, CLR, or RCP can be generated by transcription in vivo, which involves modifying the nucleic acid molecule encoding RAMP1, CLR, or RCP for the production of dsRNA (see Evans et al., "CGRP-RCP, a Novel Protein Required for Signal Transduction at Calcitonin Gene-related Peptide and Adrenomedullin Receptors," *J. Biol. Chem.* 275(40):31438-43 (2000); Prado et al., "The Role of the CGRP-receptor Component Protein (RCP) in Adrenomedullin Receptor Signal Transduction," *Peptides* 22(11):1773-81 (2001), each of which is hereby incorporated by reference in its entirety), inserting the modified nucleic acid molecule into a suitable expression vector having the appropriate 5' and 3' regulatory nucleotide sequences operably linked for transcription and translation (as described above), and introducing the expression vector having the modified nucleic acid molecule into a suitable host cell or subject.

Alternatively, complementary antisense RNAs derived from a substantial portion of the coding region of the RAMP1, CLR, or RCP nucleic acid molecule are synthesized in vitro (Fire et al., "Specific Interference by Ingested dsRNA," *Nature* 391:806-811 (1998); Montgomery et al, "RNA as a Target of Double-Stranded RNA-Mediated Genetic Interference in *Caenorhabditis elegans*," *Proc Natl Acad Sci USA* 95:15502-15507; Tabara et al., "RNAi in *C. elegans*: Soaking in the Genome Sequence," *Science* 282: 430-431 (1998), each of which is hereby incorporated by reference in its entirety), and the resulting antisense RNAs are annealed in an injection buffer, and dsRNA is administered to the subject using any method of administration described herein.

iRNA for CGRP or RCP, RAMP1, or CLR can be selected using the online GenScript Corp. online service, Promega Corp. online service, or Ambion Inc. online service. Alternatively, commercially available siRNA and shRNA are available from a number of sources, including without limitation: RCP siRNA (h), sc-45539 (Santa Cruz Biotechnology, Inc.); RCP shRNA (h), TR315681 (Origene); RAMP1 shRNA Construct, TR318934 (Origene); RAMP1 siRNA, sc-40894 (Santa Cruz Biotechnology, Inc.); CLR siRNA, sc-43705 (Santa Cruz Biotechnology, Inc.); and CLR shRNA Construct, TR314222 (Origene). In addition, the antisense DNA oligonucleotide (TGCTCACTGTGTAAGCCTTAAATC-CATCAAG; SEQ ID NO:9) has been shown to inhibit CGRP receptor function in the oocyte-CFTR assay described in Luebke et al., "Identification of a Protein that Confers Calcitonin Gene-related Peptide Responsiveness to Oocytes by Using a Cystic Fibrosis Transmembrane Conductance Regulator Assay," *Proc Natl Acad Sci USA* 93(8):3455-60 (1996), which is hereby incorporated by reference in its entirety.

As noted above, the various CGRP antagonists are intended to be introduced into a patient to achieve their therapeutic effect in treating cancer. Administration of the CGRP antagonist can be achieved by any means suitable to achieve delivery of the agent to the desired cells, and such administration can be carried out systemically or via direct or local administration, i.e., to a tumor site. By way of example, suitable modes of systemic administration include, without limitation, orally, topically, transdermally, parenterally, subcutaneously, intravenously, intramuscularly, intraperitoneally, by intranasal instillation, by intracavitary or intravesical instillation, intraocularly, intraarterially, intralesionally, or by application to mucous membranes. Suitable modes of local administration include, without limitation, catheterization, implantation, direct injection, dermal/transdermal application, stenting, ear/eye drops, or portal vein administration to relevant tissues, or any other local administration technique, method or procedure, as is generally known in the art.

With respect to the administration of small molecule inhibitors and protein inhibitors, these materials can be administered in the form of a pharmaceutical composition that includes a pharmaceutically acceptable carrier and one or more of the active agents. As noted above, exemplary pharmaceutical carriers are described in the literature, cited herein, describing the various agents per se. Antibodies are generally stable and can be administered in a suitable diluent. Protein inhibitors can also be present in the form of a conjugate that reduces the degradation thereof in vivo.

iRNA and nucleic acid aptamers are preferably administered alone or as a component of a composition. Suitable compositions include the nucleic acid formulated or complexed with polyethylenimine (e.g., linear or branched PEI) and/or polyethylenimine derivatives, including for example grafted PEIs such as galactose PEI, cholesterol PEI, antibody derivatized PEI, and polyethylene glycol PEI (PEG-PEI) derivatives thereof (see, e.g., Blazek-Welsh & Rhodes, "Maltodextrin-based Proniosomes," *AAPS Pharm. Sci.* 3(1):1-11 (2001); Furgeson et al., "Modified Linear Polyethylenimine-cholesterol Conjugates for DNA Complexation," *Bioconjug. Chem.* 14:840-7 (2003); Kunath et al., "The Structure of PEG-modified Poly(Ethylene Imines) Influences Biodistribution and Pharmacokinetics of Their Complexes with NF-κB Decoy in Mice," *Pharm. Res.* 19:810-7 (2002); Choi et al., "Effect of Poly(Ethylene Glycol) Grafting on Polyethylenimine as a Gene Transfer Vector in Vitro," *Bull. Korean Chem. Soc.* 22(1):46-52 (2001); Bettinger et al., "Size Reduction of Galactosylated PEI/DNA Complexes Improves Lectin-mediated Gene Transfer into Hepatocytes," *Bioconjug. Chem.* 10:558-61 (1999); Petersen et al., "Polyethylenimine-graft-poly(ethylene glycol) Copolymers: Influence of Copolymer Block Structure on DNA Complexation and Biological Activities as Gene Delivery System," *Bioconjug. Chem.* 13:845-54 (2002); Erbacher et al., "Transfection and Physical Properties of Various Saccharide, Poly(Ethylene Glycol), and Antibody-derivatized Polyethylenimines (PEI)," *J. Gene Med.* 1(3):210-22 (1999); Godbey et al., "Tracking the Intracellular Path of Poly(Ethylenimine)/DNA Complexes for Gene Delivery," *Proc. Natl. Acad. Sci. USA* 96:5177-81 (1999); Godbey et al., "Poly(Ethylenimine) and Its Role in Gene Delivery," *J. Control. Release* 60:149-60 (1999); Diebold et al., "Mannose Polyethylenimine Conjugates for Targeted DNA Delivery into Dendritic Cells," *J. Biol. Chem.* 274:19087-94 (1999); Thomas & Klibanov, "Enhancing Polyethylenimine's Delivery of Plasmid DNA into Mammalian Cells," *Proc. Nat'l Acad. Sci. USA* 99:14640-5 (2002); and U.S. Pat. No. 6,586,524 to Sagara, each of which is hereby incorporated by reference in its entirety.

The iRNA molecule can also be present in the form of a bioconjugate, for example a nucleic acid conjugate as described in U.S. Pat. Nos. 6,528,631, 6,335,434, 6,235,886, 6,153,737, 5,214,136, or 5,138,045, each of which is hereby incorporated by reference in its entirety.

The iRNA, or any composition or bioconjugate containing the same, can also be administered via a liposomal delivery mechanism. Basically, this involves providing a liposome which includes the siRNA to be delivered, and then contacting the target cancer cell with the liposome under conditions effective for delivery of the iRNA into the cancer cell. Again, for administration to a primary tumor site, the liposomal vesicles need not be targeted to the cancer cells per se. However, where the cancer cells to be treated include metastatic cells and possible multiple secondary tumor sites, then it is desirable to administer liposomes that are targeted for delivery to the cancer cells per se. The liposome delivery system can be made to accumulate at a target organ, tissue, or cell via active targeting (e.g., by incorporating an antibody or hormone on the surface of the liposomal vehicle). This can be achieved using antibodies specific for an appropriate cancer cell marker.

Different types of liposomes can be prepared according to Bangham et al., "Diffusion of Univalent Ions across the Lamellae of Swollen Phospholipids," *J. Mol. Biol.* 13:238-252 (1965); U.S. Pat. No. 5,653,996 to Hsu et al.; U.S. Pat. No. 5,643,599 to Lee et al.; U.S. Pat. No. 5,885,613 to Holland et al.; U.S. Pat. No. 5,631,237 to Dzau et al.; and U.S. Pat. No. 5,059,421 to Loughrey et al., each of which is hereby incorporated by reference in its entirety.

These liposomes can be produced such that they contain, in addition to iRNA, other therapeutic agents, such as anti-inflammatory agents, chemotherapeutic agents, or immune-enhancing agents (e.g., IL-2 or interferon alpha or GM-CSF), which would also be released at the target site (e.g., Wolff et al., "The Use of Monoclonal Anti-Thyl-IgG1 for the Targeting of Liposomes to AKR-A Cells in vitro and in vivo," *Biochem. Biophys. Acta* 802:259 (1984), which is hereby incorporated by reference in its entirety).

As an alternative to non-infective delivery of the inhibitory RNA as described above, naked DNA or infective transformation vectors can be used for delivery, whereby the naked DNA or infective transformation vector contains a recombinant gene that encodes the inhibitory RNA capable of inhibiting expression of RAMP1, CLR, or RCP. The inhibitory RNA molecule is then expressed in the transformed cell.

The recombinant gene includes, operatively coupled to one another, an upstream promoter operable in mammalian cells and optionally other suitable regulatory elements (i.e., enhancer or inducer elements), a coding sequence that encodes the therapeutic nucleic acid (described above), and a downstream transcription termination region. Any suitable constitutive promoter or inducible promoter can be used to regulate transcription of the recombinant gene, and one of skill in the art can readily select and utilize such promoters, whether now known or hereafter developed. The promoter can also be made inducible/repressible using, e.g., a TetO response element. Other inducible elements can also be used. Known recombinant techniques can be utilized to prepare the recombinant gene, transfer it into the expression vector (if used), and administer the vector or naked DNA to a patient. Exemplary procedures are described in SAMBROOK & RUSSELL, MOLECULAR CLONING: A LABORATORY MANUAL (2d ed. 1989), which is hereby incorporated by reference in its entirety. One of skill in the art can readily modify these procedures, as desired, using known variations of the procedures described therein.

Any suitable viral or infective transformation vector can be used. Exemplary viral vectors include, without limitation, adenovirus, adeno-associated virus, and retroviral vectors (including lentiviral vectors).

Adenovirus gene delivery vehicles can be readily prepared and utilized given the disclosure provided in Berkner, "Development of Adenovirus Vectors for Expression of Heterologous Genes," *Biotechniques* 6:616-627 (1988); Rosenfeld et al., "Adenovirus-Mediated Transfer of a Recombinant α1-Antitrypsin Gene to the Lung Epithelium in vivo," *Science* 252:431-434 (1991); PCT Publication No. WO 93/07283; PCT Publication No. WO 93/06223; and PCT Publication No. WO 93/07282, each of which is hereby incorporated by reference in its entirety. Additional types of adenovirus vectors are described in U.S. Pat. No. 6,057,155 to Wickham et al.; U.S. Pat. No. 6,033,908 to Bout et al.; U.S.

Pat. No. 6,001,557 to Wilson et al.; U.S. Pat. No. 5,994,132 to Chamberlain et al.; U.S. Pat. No. 5,981,225 to Kochanek et al.; U.S. Pat. No. 5,885,808 to Spooner et al.; and U.S. Pat. No. 5,871,727 to Curiel, each of which is hereby incorporated by reference in its entirety.

Adeno-associated viral gene delivery vehicles can be constructed and used to deliver into cells a recombinant gene encoding a desired nucleic acid. The use of adeno-associated viral gene delivery vehicles in vitro is described in Chatterjee et al., "Dual-Target Inhibition of HIV-1 in vitro by Means of an Adeno-Associated Virus Antisense Vector," *Science* 258: 1485-1488 (1992); Walsh et al., "Regulated High Level Expression of a Human Gamma-globin Gene Introduced into Erythroid Cells by an Adeno-associated Virus Vector," *Proc. Nat'l Acad. Sci. USA* 89:7257-7261 (1992); Walsh et al., "Phenotypic Correction of *Fanconi anemia* in Human Hematopoietic Cells with a Recombinant Adeno-associated Virus Vector," *J. Clin. Invest.* 94:1440-1448 (1994); Flotte et al., "Expression of the Cystic Fibrosis Transmembrane Conductance Regulator from a Novel Adeno-Associated Virus Promoter," *J. Biol. Chem.* 268:3781-3790 (1993); Ponnazhagan et al., "Suppression of Human Alpha-globin Gene Expression Mediated by the Recombinant Adeno-associated Virus 2-based Antisense Vectors," *J. Exp. Med.* 179:733-738 (1994); Miller et al., "Recombinant Adeno-Associated Virus (Raav)-Mediated Expression of a Human Gamma-Globin Gene in Human Progenitor-Derived Erythroid Cells," *Proc. Nat'l Acad. Sci. USA* 91:10183-10187 (1994); Einerhand et al., "Regulated High-Level Human Beta-Globin Gene Expression in Erythroid Cells Following Recombinant Adeno-Associated Virus-Mediated Gene Transfer," *Gene Ther.* 2:336-343 (1995); Luo et al., "Adeno-Associated Virus 2-Mediated Gene Transfer and Functional Expression of the Human Granulocyte-Macrophage Colony-Stimulating Factor," *Exp. Hematol.* 23:1261-1267 (1995); and Zhou et al., "Adeno-associated Virus 2-Mediated Transduction and Erythroid Cell-Specific Expression of a Human Beta-Globin Gene," *Gene Ther.* 3:223-229 (1996), each of which is hereby incorporated by reference in its entirety. In vivo use of these vehicles is described in Flotte et al., "Adeno-associated Virus 2-Mediated Transduction and Erythroid Cell-Specific Expression of a Human Beta-Globin Gene," *Proc. Nat'l Acad. Sci. USA* 90:10613-10617 (1993); and Kaplitt et al., "Long-term Gene Expression and Phenotypic Correction using Adeno-associated Virus Vectors in the Mammalian Brain," *Nature Genet.* 8:148-153 (1994), each of which is hereby incorporated by reference in its entirety.

Retroviral vectors which have been modified to form infective transformation systems can also be used to deliver a recombinant gene encoding a desired nucleic acid product into a target cell. One such type of retroviral vector is disclosed in U.S. Pat. No. 5,849,586 to Kriegler et al., which is hereby incorporated by reference in its entirety. Lentivirus vectors can also be utilized, including those described in U.S. Pat. No. 6,790,657 to Arya, and U.S. Patent Application Nos. 20040170962 to Kafri et al. and 20040147026 to Arya, each of which is hereby incorporated by reference in its entirety.

The various gene therapy approaches for introducing CGRP antagonists (peptides or inhibitory nucleic acids) to cancer cells are intended to be introduced into a patient to achieve their therapeutic effect in treating cancer. Administration of these CGRP antagonists can be achieved by any means suitable to achieve delivery of the agent to the desired cells, and such administration can be carried out systemically or via direct or local administration, i.e., to a tumor site. Suitable modes of systemic and local administration include those identified for administration of small molecule or polypeptide or nucleic acid aptamer CGRP antagonists.

The amount of the CGRP antagonist to be administered can vary depending upon the mode of administration and the nature of the cancer cells being targeted, but preferably the dosage is between about 0.01 to about 10 mg/kg·body weight, more preferably between about 30 to about 300 µg/kg·body weight. This dosage can optionally be repeated periodically, for instance, up to several times daily or weekly as needed during the course of treatment. Continuous pump dosages can also be used to introduce a steady-state of the CGRP antagonist during a prolonged course of treatment, i.e., over several weeks up to several months or longer as needed.

It is also contemplated that the CGRP antagonists of the present invention can be administered in combination with one or more other therapeutic agents. For example, the CGRP antagonists can be administered in combination or contemporaneously with a chemotherapeutic agent suitable for a particular type of cancer, radiation therapy, an immune-enhancing agent (e.g., IL-2 or interferon alpha or GM-CSF), or an anti-angiogenic factor.

A further aspect of the present invention relates to a method of screening compounds for inhibition of calcitonin-gene related peptide ("CGRP") receptor function. The method includes the steps of contacting a cell (preferably a eukaryotic cell) that expresses the CGRP receptor with a test agent; and determining the effect, if any, of the test agent on CGRP receptor function, or the effect on protein-protein interactions between CLR and RAMP1, CLR and RCP, and RAMP1 and RCP. Compounds identified as inhibitors of CGRP receptor activity, or of the interactions among the CGRP receptor constituent proteins, can also be utilized in the above-identified methods of treating cancer.

The cell used in the above assay can be any CGRP-expressing eukaryotic cell, one example of which is an NIH3T3 cell.

According to one embodiment, the CGRP receptor activity can be screened by measuring the level of cAMP production, which can be readily determined using a biochemical assay. Diminished cAMP production in the presence of CGRP and the test compound, when compared to cAMP product in the presence of CGRP alone, indicates that the agent is a CGRP antagonist.

According to another embodiment, the interactions among the three constituent CGRP receptor proteins (CLR, RCP, and RAMP1) can be screened. This can be achieved via measurement of co-immunoprecipitation in the presence or absence of a test agent. The absence of co-immunoprecipitation in the presence of the test agent indicates that the test agent interferences with CGRP receptor function via disruption of protein-protein interactions (i.e., between CLR and RCP, between CLR and RAMP, or between RAMP and RCP). Alternatively, this can be achieved by measurement of fluorescence resonance energy transfer (FRET) or bioluminescence resonance energy transfer (BRET) using fusion receptor proteins that contain a bioluminescent label that does not itself interfere with their interaction or signaling. In a preferred embodiment of the present invention, the candidate compounds that disrupt the protein-protein interactions between components of the CGRP receptor are screened using a rapid and sensitive assay based on polarized FRET (pFRET).

In conventional intensity-based FRET imaging, the wavelength of excitation light is chosen to maximally excite the donor fluorophore and minimally excite the acceptor fluorophore. If the two fluorophores are sufficiently close (50 angstroms or less), energy imparted to the donor by the excitation laser is transferred to the acceptor and subsequently emitted as a fluorescence photon at the typical emission wavelengths of the acceptor. Thus, proximity is measured as a gain of acceptor fluorophore emission. Typical fluorophores used are cyan fluorescent protein (CFP) for the donor and yellow fluorescent protein (YFP) for the acceptor. When two test proteins are expressed as fusion proteins with CFP and YFP, protein interaction can be scored by FRET. These studies are typically carried out on a cell by cell basis using wide-field fluorescence microscopy.

There are several limitations to this conventional intensity-based method of quantifying FRET efficiency. First, "bleed-through" of donor fluorescence into the acceptor detection channel is difficult to completely eliminate due to the emission spectral overlap of the two fluorophores, and direct excitation of acceptor by the excitation laser is impossible to completely eliminate due to the overlap in excitation spectra. Both of these effects produce a false positive FRET signal. Second, the signal from the donor fluorophore and acceptor fluorophore are sufficient for traditional microscope-based FRET, but lack sufficient intensity for reliable quantification in a plate reader format. Third, microscopy-based FRET is impractical to use for screening large numbers of samples, as each cell must be individually identified, analyzed for FRET, and then background and bleed-through between donor and acceptor data channels must be corrected (Jares-Erijman et al., "FRET Imaging," *Nat Biotechnol* 21(11):1387-95 (2003), which is hereby incorporated by reference in its entirety).

To overcome the above-noted deficiencies of these conventional methods, a rapid and sensitive screening method was developed. This method involves the adaption of polarized fluorescence resonance energy transfer (pFRET) to a plate reader form to overcome the above noted deficiencies and enable high throughput screening analysis of protein-protein interactions. Fluorescence emission of the various fluorescent proteins is highly polarized, i.e. the polarization of the emitted fluorescence is highly correlated with the excitation laser's polarization. In contrast, fluorescence emitted by acceptor fluorophores after FRET energy transfer is much less correlated with the excitation polarization. This degree of correlation can be measured and anisotropy calculated r=(VV−gVH)/(VV+2gVH) (Rizzo et al., "High-Contrast Imaging of Fluorescent Protein FRET by Fluorescence Polarization Microscopy," *Biophys J* 88(2):L14-6 (2005), which is hereby incorporated by reference in its entirety), where VV is the signal in the detector polarized parallel to the laser polarization, VH is the signal in the detector polarized perpendicular to the laser polarization and g corrects for polarization bias in the detection system. An increase in FRET efficiency is manifested by a decrease in anisotropy. It is significant to note that "bleed through" of donor emission and direct excitation of acceptor by the excitation laser both cause an increase in anisotropy, and hence are no longer false positives, a key fact for high throughput screens. The pFRET assay of the present invention can be easily adapted to identify and study other protein-protein interactions, and hence provides a rapid method to discover novel compounds that can disrupt, and thus alter function.

According to a further embodiment, CGRP receptor function can be measured via interaction of RCP with CLR.

According to yet another embodiment, disruption between any two CGRP receptor proteins can be measured via the yeast two-hybrid approach. In this approach, the yeast cell expresses a first transgene that encodes a fusion protein that includes CLR or a fragment thereof fused to a prey polypeptide, and a second transgene that includes RCP or a fragment thereof fused to a bait polypeptide, or vice versa (RCP-prey and CLR-bait). Interaction of the CLR and RCP proteins or fragments thereof results in functional interaction of prey-bait, which is measured directly by expression of a reporter gene. Any suitable reporter gene can be used, including a selectable marker or fluorescent reporter genes or a product that is readily detectable by immunoassay, or other detection means.

Figure 8:
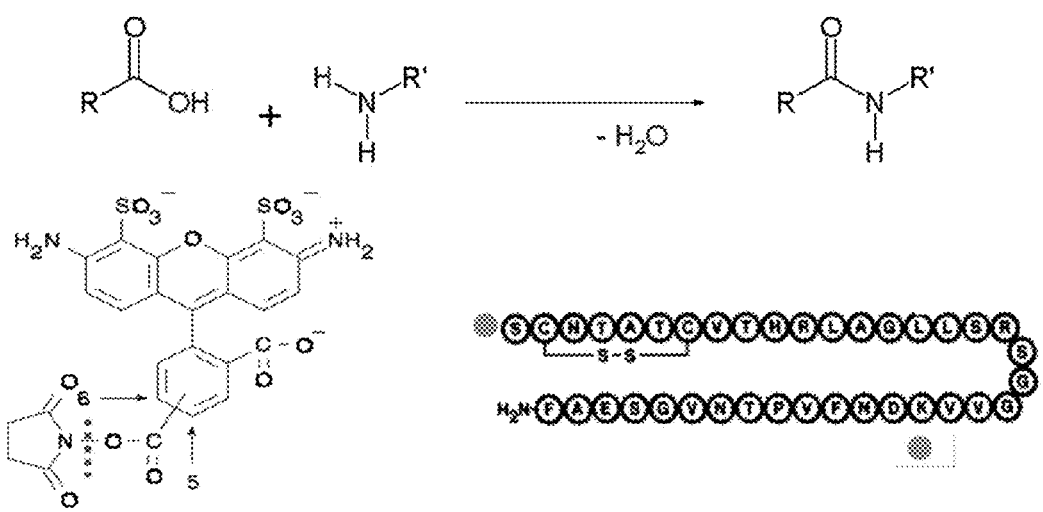
FIG. 8 illustrates a strategy for fluorescently labeling CGRP. Alexa488 dye (Molecular Probes), in the form of a succinimyl ester, can be used to label primary amines (indicated by dots) in CGRP (SEQ ID NO: 10). These amines include the N-terminal Ser residue as well as the Lys$^{24}$ residue.

Finally, according to a further embodiment, direct inhibition of CGRP binding to the CGRP receptor can be measured using competition assays or ELISA assays using a fluorescently labeled CGRP or radiolabeled CGRP. One embodiment of the fluorescently labeled CGRP is illustrated in FIG. 8 and described in the accompanying examples. This embodiment includes a single fluorophore tethered to the peptide, wherein the fluorescent CGRP is capable of binding to a CGRP receptor (i.e., the fluorophore does not interfere with CGRP-receptor binding). More particularly, the single fluorophore is tethered to residue $Lys^{24}$. This singly-labeled fluorophore can be utilized in a pure form. The competition assay or ELISA can include CGRP-binding reagent, such as an antibody or fragment thereof, that is bound to a solid surface to which the fluorescently labeled or radio labeled CGRP is introduced alone (positive control) and in competition with a suspected antagonist. A comparison of the results between positive and negative control along with the suspected antagonist will allow for a determination as to whether the suspected antagonist does, in fact, interfere with CGRP binding to the CGRP-binding reagent.

The fluorescently labeled CGRP can be prepared using a fluorophore containing a cross-reactive group (e.g., ester such as NHS ester, imidoester, or PFP ester; or carbodiimide) that can react with an available amino group or carboxyl group in CGRP. An exemplary fluorophore is an Alexa Fluor® succinimidyl ester (Invitrogen/Molecular Probes, Eugene, Oreg.), which demonstrates very low reactivity with aromatic amines, alcohols, and phenols, including tyrosine and histidine, and forms stable peptide bonds. Standard cross-linking reactions can be used depending on the selected cross-reactive group. As demonstrated in the accompanying examples, a succinimidyl ester modified fluorophore can be reacted with an amine group in CGRP (such as $Lys^{24}$) to afford a singly labeled CGRP molecule. Purification of singly-labeled CGRP from unlabeled and double-labeled CGRP was accomplished by separating the labeling mixture by reverse-phase HPLC. The labeling mixture was adjusted to 0.1% formic acid, and separated on a C18 HPLC column using an acetonitrile gradient. Buffer A was composed of 0.1% formic acid, and Buffer B was composed of 0.1% formic acid and 80% acetonitrile. Sample was injected onto the C18 column in 100% Buffer A, and Buffer B was increased in two steps; the first step took 10 minutes to reach 39% Buffer B, and the second step took 16 minutes to reach 46% Buffer B. The CGRP labeling products eluted during this second buffer step. This second step was useful for obtaining a singly-labeled CGRP that is essentially free of unlabeled CGRP and doubly-labeled CGRP. By "essentially free" it is intended that the purified singly-labeled CGRP preparation contains less than 0.5% or 0.1%, more preferably less than 0.01% or most preferably less than 0.001%, of contaminating unlabeled or doubly-labeled CGRP molecules, as determined by fourier transform mass spectrometry.

A further aspect of the present invention relates to a non-human, animal model of cancer. This animal model is preferably a mammal (e.g., rodent) and includes tumor cells introduced into the mammal, wherein the tumor cells express CGRP receptor and include a transgene expressing a fluorescent marker protein. In this animal model of cancer the introduced tumor cells are preferably derived from human tumors or human tumor cell lines, i.e., the mammal is a xenograft model of cancer, although tumor cells derived from rodent cell lines can also be used.

Figure 7:
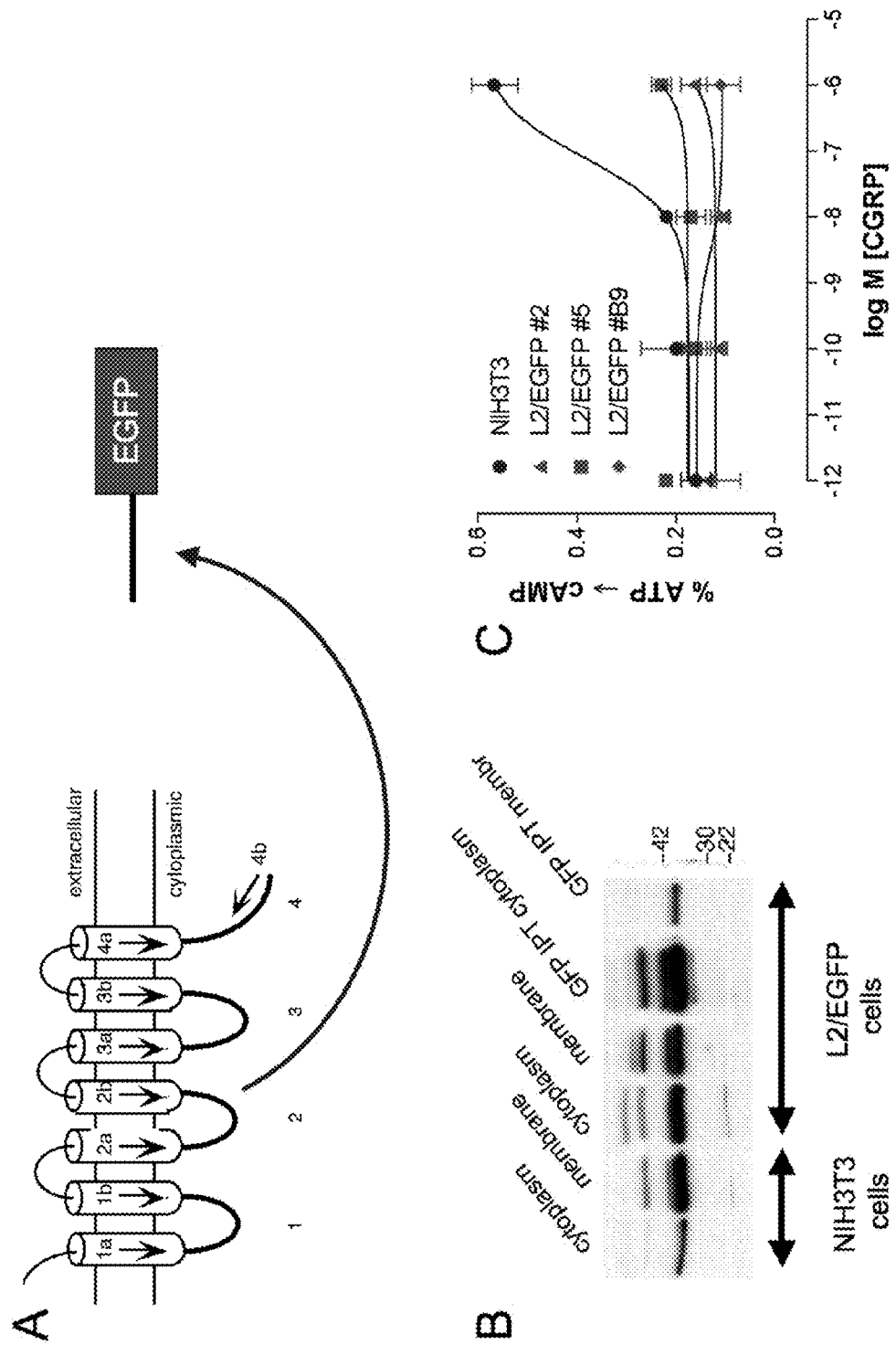
FIGS. 7A-C demonstrate that RCP interacts with the second cytoplasmic domain (cpd) of CLR in mammalian cell culture.

The tumor cells preferably contain a transgene that expresses a dominant-negative regulator of CGRP receptor function, which can be constitutively expressed or inducibly expressed using appropriate regulatory control sequences in the promoter regions of the transgene. The dominant-negative regulator of CGRP receptor function is preferably a fusion protein that includes a second cytoplasmic domain of the CLR fused to a fluorescent protein (e.g., GFP, YFP, RFP, etc.). One example of this fusion protein is illustrated in FIG. 7A, which was prepared using standard recombinant techniques for expressing the second cytoplasmic domain as an N-terminal fusion with the C-terminal EGFP. The second cytoplasmic domain corresponds to the region from residues leucine$^{240}$ to alanine$^{270}$ in the CLR of SEQ ID NO: 6, as well as corresponding homologs thereof in other mammalian CLR.

A still further aspect of the present invention relates to a transgenic cell line that expresses a dominant-negative regulator of CGRP receptor function of the type described above. This cell line can be introduced into a rodent to generate the model of disease.

According to one embodiment, the cell line can be of human origin, for example one derived from a human breast cancer cell line or a brain metastasizing human breast cancer cell line.

According to another embodiment, the cell line can be from the same or a different type of rodent, such as a rat glioma cell line.

In preferred embodiments, the transgene used to transfect the cell line includes an inducible promoter to regulate expression of the dominant-negative regulator of CGRP receptor function. Exemplary inducible promoters for use with this embodiment include, without limitation, promoters operable in mammalian cells and modified to include a TRE-regulated sequence that is stimulated by rtTA only in the presence of an unsubstituted and substituted tetracycline compound. Promoters and Tet-On systems of this type are commercially available from, e.g., Clontech (Mountain View, Calif.), and are described at, e.g., U.S. Patent Application Publ. No. 20090257985 to Nelson et al., which is hereby incorporated by reference in its entirety.

EXAMPLES

The present invention is further described with reference to the following examples, which are not intended to limit the scope of the claimed invention in any way.

Example 1

Differential Expression of Calcitonin Gene-Related Peptide Receptor in Metastatic Tumor Cells Tumor metastasis requires the successful completion of a complex series of steps, involving migration of a tumor cell towards a tumor blood vessel, entry into the blood vessel, survival in the bloodstream, lodgment in a distant vessel, and proliferation in the new site. To investigate the molecular pathways involved in influencing tumor cell metastasis, a pair of cell lines derived from breast cancer patients, MDA-MB-231 (231) and MDA-MB-231BR (231BR), and CNS1 glioma cells were utilized. The MDA-MB-231 cell line is a human estrogen-independent breast cancer cell line that metastasizes primarily to bone, but also at low frequency to brain, ovary and adrenal gland when injected into the left ventricle of the heart in nude mice (Cailleau et al., "Breast Tumor Cell Lines From Pleural Effusions," *J Natl Cancer Inst* 53(3):661-74 (1974); Yoneda T., "Cellular and Molecular Mechanisms of Breast and Prostate Cancer Metastasis To Bone," *Eur J Cancer* 34(2):240-5 (1998); Yoneda et al., "Osteolytic Bone Metastasis in Breast Cancer," *Breast Cancer Res Treat* 32(1):73-84 (1994), which are hereby incorporated by reference in their entirety). MDA-MB-231BR cells were derived from the MDA-MB-231 line by isolating cells of rare brain-metastases that developed following intracardiac injection of the MDA-MB-231 cells, and by passaging the brain-metastasizing cells through animals six times. The resulting MDA-MB-231BR cells preferentially metastasize to the brain when injected into the left ventricle of mice. CNS1 glioma cells (Kruse et al., "A Rat Glioma Model, CNS-1, with Invasive Characteristics Similar to those of Human Gliomas: A Comparison to 9L Gliosarcoma," *J. Neurooncol.* 22:191-200 (1994), which is hereby incorporated by reference in its entirety) are characterized by an aggressive invasive phenotype, and serve as a model glioma system for which to study the role of CGRP-receptor signaling in glioma tumor cell proliferation and growth.

The properties of the 231BR cell line that improve its metastatic ability compared to its parent cell line were investigated, and compared to the CNS1 cells. Analysis of the metastatic process using principles of biomedical engineering provided key insights. After vascular entry, the 231BR cells lodge in the brain vasculature. It is believed that this event is trigged by one or more cells blocking a small capillary and obstructing blood flow to the tissue surrounding that capillary (the Krogh cylinder), which exposes the tumor cells to hypoxia. Because subsequent proliferation occurs under hypoxia, it was believed that the molecular pathways that were differentially regulated in the 231 and 231BR cell lines under hypoxia were promising candidates for pathways that play a key role in metastasis. Therefore, a proteomic screen was performed to identify proteins that were differentially expressed in these two cell lines under hypoxia, and the expression levels of several candidate proteins were validated by western blot analysis. This analysis revealed that an element of the Calcitonin Gene-Related Peptide Receptor (CGRPR) was differentially regulated.

The CGRPR is a unique G-coupled receptor consisting of a core transmembrane calcitonin-like receptor (CLR) protein and two accessory proteins (FIG. 1). The first accessory protein is the transmembrane Receptor Activity Modifying Protein (RAMP1), which is responsible for intracellular trafficking of CLR to the cell surface and pharmacologic specificity. There are three forms of RAMP. CLR plus RAMP1 generates a high-affinity receptor for the neuropeptide Calcitonin Gene-Related Peptide (CGRP), while CLR plus RAMP2 or RAMP3 forms a high-affinity receptor for the neuropeptide adrenomedullin (McLatchie et al., "RAMPs Regulate the Transport and Ligand Specificity of the Calcitonin-Receptor-Like Receptor," *Nature* 393(6683):333-9 (1998), which is hereby incorporated by reference in its entirety). The second accessory protein is CGRP-receptor component protein (RCP), which couples the CLR/RAMP complex to the cellular signaling pathway (Evans et al., "CGRP-RCP, A Novel Protein Required for Signal Transduction at Calcitonin Gene-Related Peptide and Adrenomedullin Receptors," *J Biol Chem* 275(40):31438-43 (2000) and Prado et al., "The Role of the CGRP-Receptor Component Protein (RCP) in Adrenomedullin Receptor Signal Transduction," *Peptides* 22(11):1773-81 (2001), which are hereby incorporated by reference in their entirety).

Figure 2:
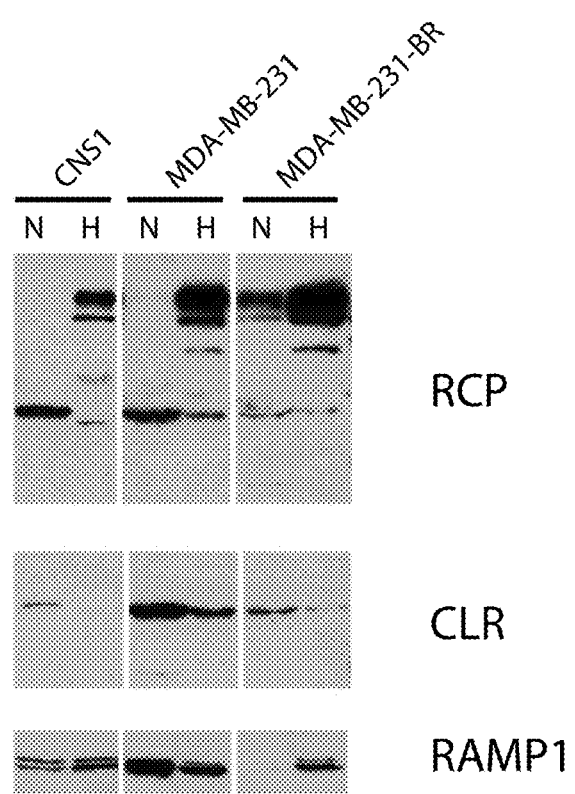
FIG. 2 shows western blot results of RCP, CLR, and RAMP1 protein expression in MDA-MB-231 breast cancer cells, MDA-MB-231 BR breast cancer cells, and CNS1 glioma cells under normoxic ("N") and hypoxic ("H") conditions. RAMP1 (~38 kDa) expression is differentially regulated in MDA-MB231 cells compared to MDA-MB-231BR cells. CLR (~55 kDa) expression is downregulated by hypoxia in all cell types, while RCP (~55 kDa, but appearing as its typical ~300 kDa molecular weight multimer (Prado et al., "The Role of the CGRP-Receptor Component Protein (RCP) in Adrenomedullin Receptor Signal Transduction," *Peptides* 22:1773-81 (2001), which is hereby incorporated by reference in its entirety)) expression is upregulated by hypoxia in all three cells types.

Expression of the CGRP receptor proteins is complex. Under hypoxic conditions, expression of RCP is significantly increased—primarily the high molecular weight form—in both 231 and 231BR tumor cells (FIG. 2). Similarly, the high molecular weight form of RCP is also increased in CNS1 cells under hypoxic conditions (FIG. 2). In contrast to RCP, RAMP1 does not appear to be uniformly regulated under hypoxic conditions. RAMP1 expression is increased in 231BR cells under hypoxia and decreased in the parent 231 cells, and a modest increase is seen in CNS1 cells (FIG. 2). Expression of CLR is uniformly reduced in 231, 231BR, and CNS1 cells.

Example 2

CGRP Stimulates Glioma and Breast Tumor Cell Proliferation and Growth

Elevated expression of RCP or RAMP1 under hypoxic conditions will increase the number of functional CGRPRs and hence enhance a cell's response to CGRP. Trigeminal nerves innervating the cerebral vasculature express CGRP (Uddman et al., "Innervation of the Feline Cerebral Vasculature by Nerve Fibers Containing Calcitonin Gene-Related Peptide: Trigeminal Origin and Co-existence With Substance," *P. Neurosci Lett* 62:131-6 (1985), which is hereby incorporated by reference in its entirety), providing a ready source of receptor activation. Therefore, it is possible that upon vessel plugging and resultant hypoxia, subsequent tumor growth is enhanced by CGRPR activation in 231BR cells relative to 231 cells, and likewise with glioma cells.

Figures 3A, 3B:
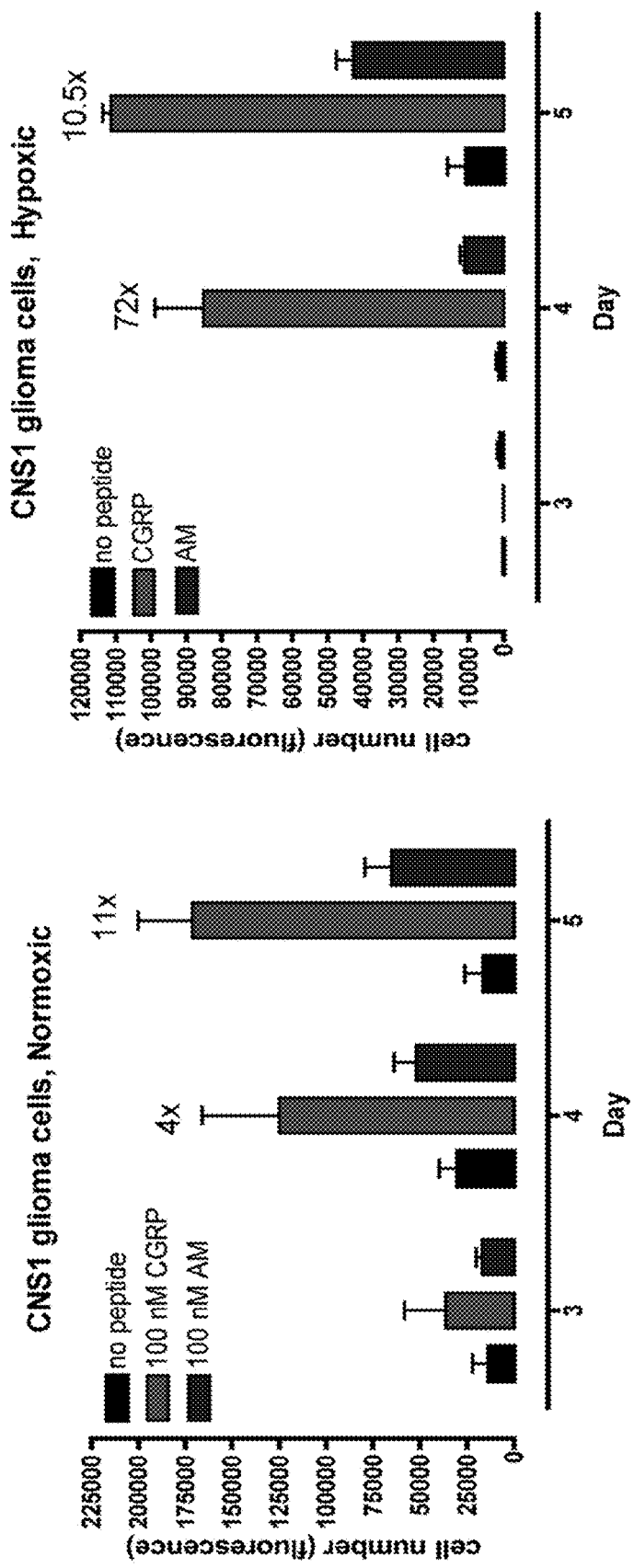
FIGS. 3A-B are graphs illustrating that CGRP is a potent stimulator of CNS1 glioma cell growth. CNS1 cells were seeded in 96-well plates, and grown for the indicated time in either normoxic (3A) or hypoxic (34B) conditions. Media was replaced every 24 hrs with fresh peptide-containing media. On each day, cell number was determined using the CyQuant Direct Proliferation Assay (Invitrogen).

The rat glioma cell line CNS1 was used in a tumor cell proliferation assay. Both AM and CGRP were tested for their ability to stimulate glioma growth. It was observed that CGRP had a dramatic effect, increasing CNS1 cell growth 4-fold (400%) over control under normoxic conditions after 4 days in culture, and 11-fold after 5 days in culture (FIG. 3A). More striking was the effect under hypoxic conditions, where CGRP stimulated glioma growth 72-fold over control after 4 days in culture and 10-fold after 5 days in culture (FIG. 3B).

The hypoxic effects are particularly important, because a key phase of solid tumor development requires growth under hypoxic conditions before the tumor can recruit new blood vessels by angiogenesis. Furthermore, tumors that can grow under hypoxic conditions are often resistant to radiotherapy, show a more advanced malignancy, and higher rates of metastasis (Brizel et al., "Tumor Oxygenation Predicts for the Likelihood of Distant Metastases in Human Soft Tissue Sarcoma," *Cancer Ress.* 56:941-943 (1996); Hockel et al., "Association Between Tumor Hypoxia and Malignant Progression in Advanced Cancer of the Uterine Cervix," *Cancer Res.* 56:4509-4515 (1996); Hockel et al., "Hypoxia and Radiation Response in Human Tumors," *Semin Radiat Oncol* 6:3-9 (1996); Nordsmark et al., "Pretreatment Oxygenation Predicts Radiation Response in Advanced Squamous Cell Carcinoma of the Head and Neck," *Radiother Oncol.* 41:31-39 (1996), each of which is hereby incorporated by reference in its entirety.

Figure 4B:
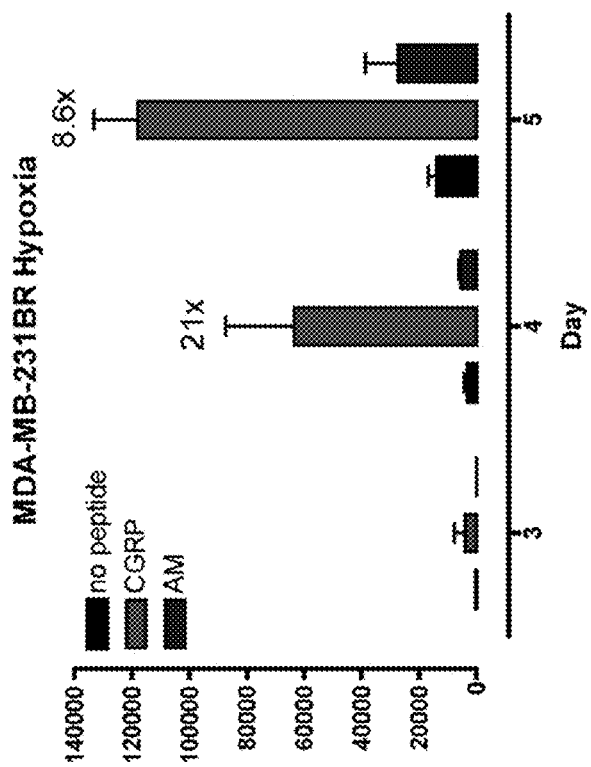
FIGS. 4A-B are graphs illustrating that CGRP is a potent stimulator of MDA-MB231BR breast cancer cell growth. MDA-MB231BR cells were seeded in 96-well plates, and grown for the indicated time in either normoxic (4A) or hypoxic (4B) conditions. Media was replaced every 24 hrs with fresh peptide-containing media. On each day, cell number was determined using the CyQuant Direct Proliferation Assay (Invitrogen).
Figure 4A:
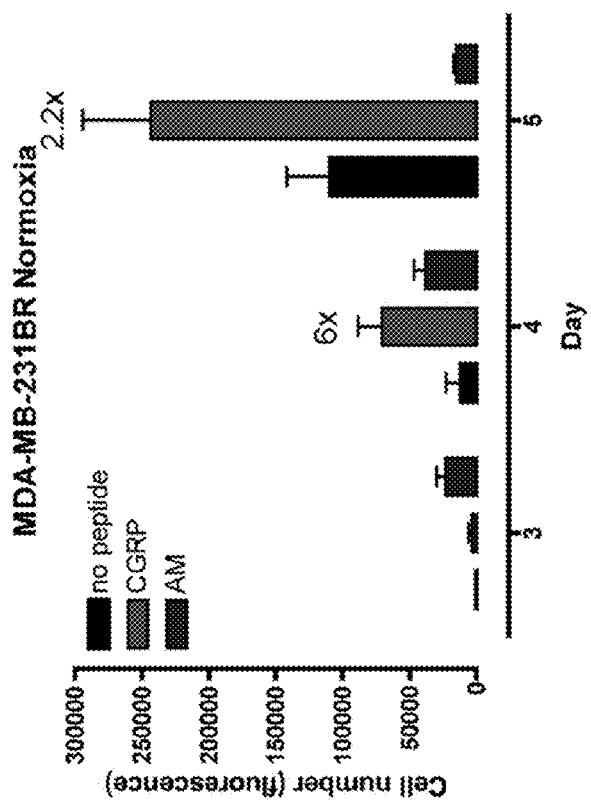

A similar role for CGRP in the stimulation of breast cancer cell growth was observed using the MDA-MB-231BR breast cancer cell line. As noted previously, MDA-MB-231 BR breast cancer cells preferentially metastasize to the brain when injected intraventricularly, and represent a model system for breast cancer that metastasizes to the brain (Yoneda et al., "A Bone-seeking Clone Exhibits Different Biological Properties from the MDA-MB-231 Parental Human Breast Cancer Cells and a Brain-seeking Clone in vivo and in vitro," *J. Bone Miner. Res.* 16:1486-1495 (2001); Palmieri et al., "Her-2 Overexpression Increases the Metastatic Outgrowth of Breast Cancer Cells in the Brain," *Cancer Res.* 67:4190-4198 (2007); Schmid et al., "The Neuronal Guidance Cue Slit2 Induces Targeted Migration and May Play a Role in Brain Metastasis of Breast Cancer Cells," *Breast Cancer Res Treat* 106:333-342 (2007); Stark et al., "Differential Expression of Matrix Metalloproteinases in Brain- and Bone-seeking Clones of Metastatic MDA-MB-231 Breast Cancer Cells," *J. Neurooncol.* 81:39-48 (2007); Oxmann et al., "Endoglin Expression in Metastatic Breast Cancer Cells Enhances Their Invasive Phenotype," *Oncogene* 27:3567-3575 (2008), each of which is herbey incorporated by reference in its entirety). In this assay, CGRP induced the MDA-MB-231BR breast cancer cells 6-fold over control after 4 days in culture under normoxic conditions (FIGS. 4A-B).

Thus, the above data confirm that CGRP stimulation promotes proliferation of gliomas as well as breast cancer cells that metastasize to the brain, and highlights that the blocking CGRP receptors represents an important new strategy for inhibiting growth of several types of cancers.

Example 3

Dominant Negative Inhibition of CLR Disrupts CGRP Receptor Signaling

CGRP appears to be a hypoxic-specific activator of breast cancer and glioma cell growth. This is important as there are currently few effective therapies for hypoxic tumors, which are aggressive and lethal. Interestingly, CGRP promotes growth of breast cancer cells destined for metastasis to the brain, and may be diagnostic for brain metastasis. Thus, the receptor for CGRP is an important target for managing breast cancer, and expression of the receptor proteins could be used as an early indicator of later metastatic events.

CLR is a core protein of the CGRPR, and inhibition of CLR will inhibit CGRP mediated receptor activation as well as activation by other neuropeptides (e.g., adrenomedullin), thereby blocking potentially multiple avenues of breast cancer metastasis.

Figure 5:
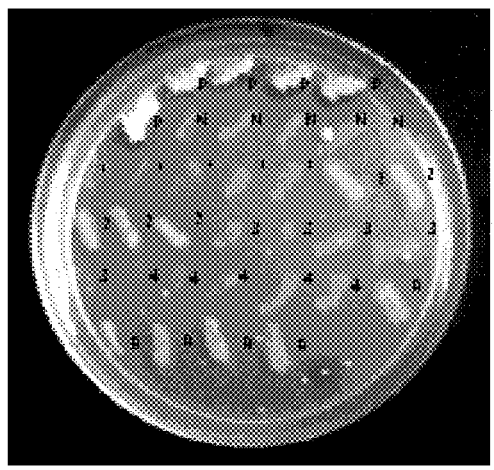
FIG. 5 is an image of a plate illustrating yeast-two hybrid experiments. Yeasts were cotransformed with RCP and the CLR cytoplasmic domains (cpd) or controls. Colonies were picked onto a master plate and replica plated onto a Leu-Trp-His plate supplemented with 3-AT. P=positive control for two-hybrid interaction using p53 and the SV40 large T antigen. N=negative control for two-hybrid interaction using lamin C protein and the T antigen. RCP cotransformed with the first cytoplasmic loop (1), second cytoplasmic loop (2), third cytoplasmic loop (3), or the carboxyl tail (4) of the CLR (see FIG. 1 for designated loops/tail). RCP was also cloned into the AD plasmid and tested against RCP in the BD plasmid (R). Active growing yeast were only observed for the positive control (P), RCP with the second cytoplasmic loop of CLR (2), and for RCP with RCP (R). Only residual yeast from the replica-plating are present for interactions between RCP and cytoplasmic loops 1 and 3, and tail 4 of the CLR.
Figure 6:
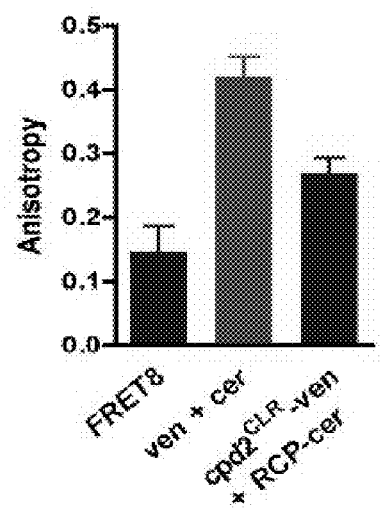
FIG. 6 is a graph showing the interaction between RCP and cpd2$^{CLR}$.detected by polarized fluorescence resonance energy transfer (pFRET). NIH3T3 cells were transfected with RCP-cerulean and cpd2$^{CLR}$—venus fusion proteins and the interaction was detected by a loss in anisotropy. NIH3T3 cells transfected with a FRET8 plasmid, in which cerulean and venus fluorophores are separated by 8 amino acids, were used as a positive control and cells co-transfected with cerulean and venus constructs that do not interact were used as negative controls.

A method to inhibit CLR was developed based on its unique multi-protein requirements. Because CLR requires RCP for signaling (Evans et al., "CGRP-RCP, A Novel Protein Required for Signal Transduction at Calcitonin Gene-Related Peptide and Adrenomedullin Receptors," *J Biol Chem* 275(40):31438-43 (2000); and Prado et al., "The Role of the CGRP-Receptor Component Protein (RCP) in Adrenomedullin Receptor Signal Transduction," *Peptides* 22(11):1773-81 (2001), which are hereby incorporated by reference in their entirety), a yeast two-hybrid screen was carried out and it was discovered that RCP interacts directly with the second cytoplasmic loop of CLR (FIGS. 5 and 6).

A fusion protein was constructed containing the second intracellular loop ("L2" or elsewhere designated "cpd2") of CLR and the enhanced green fluorescent protein (L2/EGFP) (FIG. 7A). RCP co-immunoprecipitated with the L2/EGFP fusion protein, indicating a direct interaction between the two proteins (FIG. 7B). Furthermore, when L2/EGFP was expressed in NIH3T3 cells, which endogenously express CGRP receptors, expression of L2/EGFP inhibited signaling at the CGRP receptor as measured by cAMP (FIG. 7C). This confirmed the belief that over-expression of L2/EGFP pulls most of the available RCP away from the CGRP receptor complex, and that the CLR/RAMP1 complex is unable to signal. Thus, the site of interaction between the second intracellular loop of CLR and RCP represents a novel control site for signaling at CLR, and represents a candidate for development of anti-proliferative drugs to combat tumor growth.

To determine if the dominant-negative L2/EGFP fusion protein could inhibit CLR function in breast cancer cells, four breast cancer lines (human MDA-MB-231 and MDA-MB-231 BR lines and mouse 4T1 and TG1 lines) were transfected with L2/EGFP or GFP alone. MDA-MB231 and MDA-MB-231BR cells that constitutively express GFP were generated as previously described (Evans et al., "CGRP-RCP, a Novel Protein Required for Signal Transduction at Calcitonin Gene-Related Peptide and Adrenomedullin Receptors," *J Biol Chem* 275(40):31438-43 (2000); Prado et al., "The Role of the CGRP-Receptor Component Protein (RCP) in Adrenomedullin Receptor Signal Transduction," *Peptides* 22(11):1773-81 (2001); and Rosenblatt et al., "Endoproteolysis at Tetrabasic Amino Acid Sites in Procalcitonin Gene-Related Peptide by Pituitary Cell Lines" *Peptides* 18(4):567-76 (1997), which are hereby incorporated by reference in their entirety). However, when a constitutive promoter was used to express L2/EGFP in these tumor cells, pure fluorescent colonies could not be isolated because, it is believed, the constitutive expression of L2/EGFP was too effective at inhibiting tumor growth. When mixed colonies were purified by fluorescence activated cell sorting (FACS), pure populations of cells expressing the dominant-negative inhibitor were obtained, but would not grow, indicating the potency of CLR inhibition in controlling tumor growth. These same results were obtained from multiple replicate experiments, thereby confirming that the dominant-negative inhibitor was responsible for these results.

Therefore, a tetracycline-repressible promoter will be employed to inhibit expression of L2/EGFP during cell culturing. L2/EGFP will be cloned into the tetracycline-responsive plasmid pTRE-Tight (Clontech), and this plasmid (pTRE.L2/EGFP) will be co-transfected with the plasmid pTet-Off (Clontech) into the four breast cancer tumor lines. The latter plasmid expresses the tetracycline activator protein that upon binding of tetracycline represses the TRE promoter, inhibiting expression of L2/EGFP. The pTet-Off plasmid contains the gene for geneticin resistance, while pTRE does not. The presence of pTet-Off will be selected for by growth in the presence of geneticin, and for pTRE.L2/EGFP by fluorescence in the absence of doxycycline. Once geneticin-resistant colonies are identified, colonies will be switched into doxycycline (a tetracycline analog)-deficient media, and colonies expressing L2/EGFP will be identified by fluorescence.

The inhibitory effect of L2/EGFP on CLR signaling will be tested by inducing L2/EGFP expression with the removal of doxycycline from the growth media overnight, incubating transfected cells (MDA-MB-231, MDA-MB-231BR, 4T1 and TG1) with CGRP, and assaying for cAMP response.

Example 4

CGRP Stimulates Glioma Tumor Cell Proliferation and Growth

Rat CNS1 glioma cells (Kruse et al., "A Rat Glioma Model, CNS-1, with Invasive Characteristics Similar to those of Human Gliomas: A Comparison to 9L Gliosarcoma," *J. Neurooncol.* 22:191-200 (1994), which is hereby incorporated by reference in its entirety), which are characterized by an aggressive invasive phenotype, serve as a model glioma system for which to study the role of CGRP-receptor signaling in glioma tumor cell proliferation and growth. As demonstrated in Example 2 above, CGRP is a potent activator of glioma tumor cell proliferation. Therefore, inhibitors of CGRP receptor function should be useful for anti-glioma therapy.

To examine the role of CLR in glioma proliferation, inhibition of CLR via expression of L2/EGFP was attempted. Although CNS1 cells that constitutively express GFP were generated using published techniques (Evans et al., "CGRP-RCP, A Novel Protein Required for Signal Transduction At Calcitonin Gene-Related Peptide and Adrenomedullin Receptors," *J Biol Chem* 275(40):31438-43 (2000); Prado et al., "The Role of the CGRP-Receptor Component Protein (RCP) in Adrenomedullin Receptor Signal Transduction," *Peptides* 22(11):1773-81 (2001); Rosenblatt et al., "Endoproteolysis At Tetrabasic Amino Acid Sites in Procalcitonin Gene-Related Peptide by Pituitary Cell Lines," *Peptides* 18(4):567-76 (1997), which are hereby incorporated by reference in their entirety), upon transfection of the constitutively expressed L2/EGFP construct, pure fluorescent colonies could not be isolated. Similar to the observations made in breast cancer cell lines, constitutive expression of L2/EGFP was so effective at inhibiting glioma growth that when mixed colonies were purified by fluorescence activated cell sorting (FACS), the pure populations of cells expressing the dominant-negative inhibitor would not grow. This data further supports the potency of CLR inhibition in controlling glioma growth.

Example 5

Development of a Fluorescently-labeled CGRP Probe

A fluorescent probe is needed for identification, characterization and quantification of CGRP receptors in tissues and cells. CGRP had been previously labeled with fluorescent dyes, but the labeling efficiency did not appear to be sufficient to facilitate development of either sensitive binding assays or competition assays (Cottrell et al., "Localization of Calcitonin Receptor-like Receptor and Receptor Activity Modifying Protein 1 in Enteric Neurons, Dorsal Root Ganglia, and the Spinal Cord of the Rat," *J. Comp. Neurol.* 490:239-255 (2005), which is hereby incorporated by reference in its entirety).

Figure 9A:
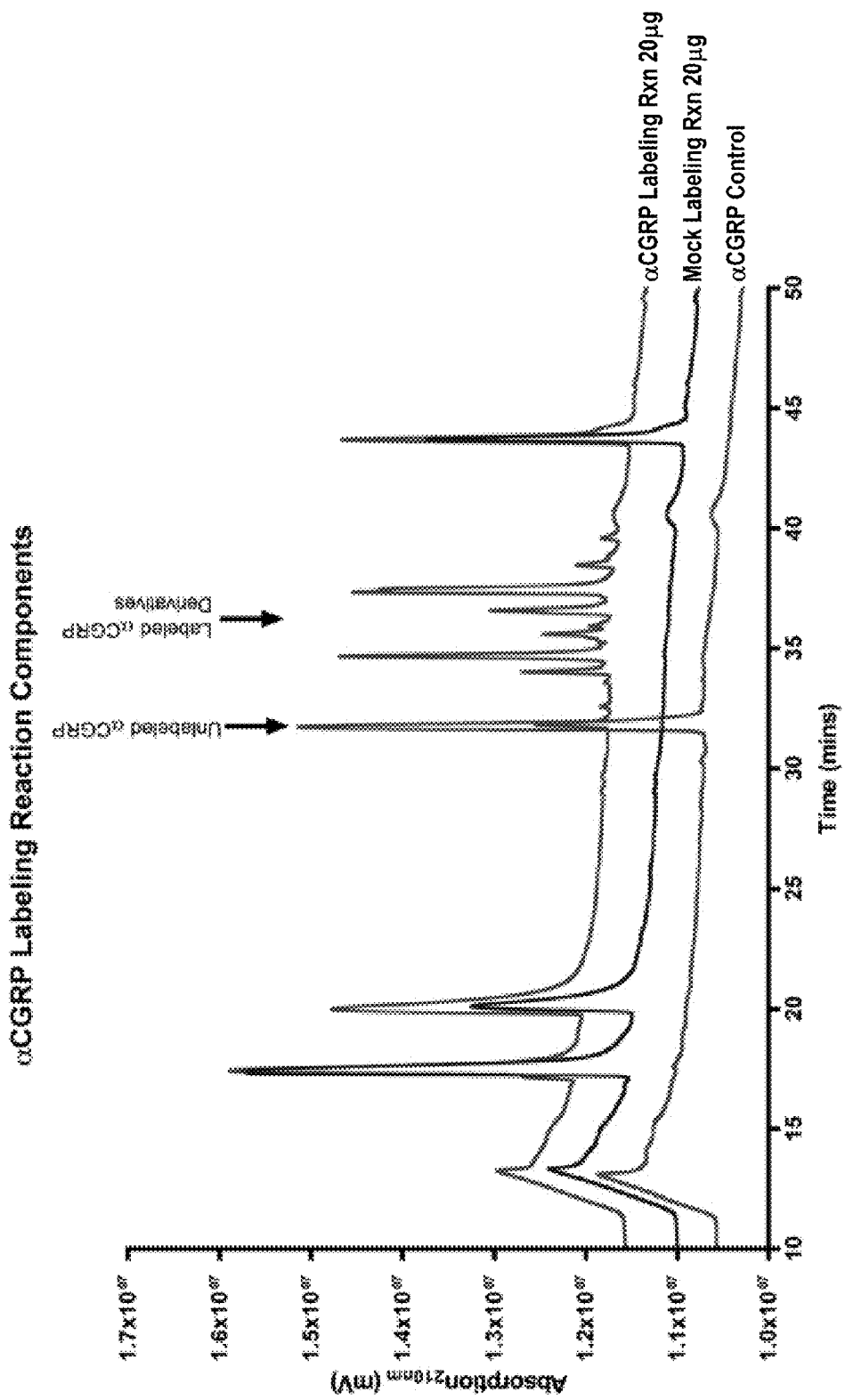
FIGS. 9A-B are graphs illustrating the identification and purification of fluorescently-labeled CGRP (FL-CGRP). Rat CGRP was labeled with Alexa488 dye, and reactants separated by RP-HPLC on a gradient of acetonitrile inn 0.1% formic acid.

Rat CGRP (SEQ ID NO: 10) was labeled using the Alexa488 dye molecule (Molecular Probes, Inc). 100 µg of CGRP was combined with 166 µg Alexa488 in a reaction volume of 100 µl at pH 8. After 60 min incubation at room temperature, the reactants were separated by reversed-phase high performance liquid chromatography (RP-HPLC) on a 4.6 mm×250 mm Waters C18 column. The labeling chemistry targets primary amines, and there are two primary amines in rat CGRP; either at the NH-terminus or at Lys$^{24}$ (FIG. 8). To maximize biological activity, it was desirable to label a single primary amine, and to purify fluorescently-labeled CGRP (FL-CGRP) away from unlabeled peptide, and labeling reactants. Fluorescently-labeled CGRP (FL-CGRP) was separated with an acetonitrile gradient in 0.1% formic acid. Buffer A was composed of 0.1% formic acid, and Buffer B was composed of 0.1% formic acid and 80% acetonitrile. The elution gradient was optimized to separate FL-CGRP from unlabeled CGRP and reaction products (FIG. 9A). The labeling mixture was adjusted to 0.1% formic acid, and separated on a C18 HPLC column using an acetonitrile gradient. Buffer A was composed of 0.1% formic acid, and Buffer B was composed of 0.1% formic acid and 80% acetonitrile. Sample was injected onto the C18 column in 100% Buffer A, and Buffer B was increased in two steps; the first step took 10 minutes to reach 39% Buffer B, and the second step took 16 minutes to reach 46% Buffer B. The CGRP labeling products eluted during this second buffer step. This second step was useful for obtaining a singly-labeled CGRP that is essentially free of unlabeled CGRP and doubly-labeled CGRP can be obtained.

Figure 9B:
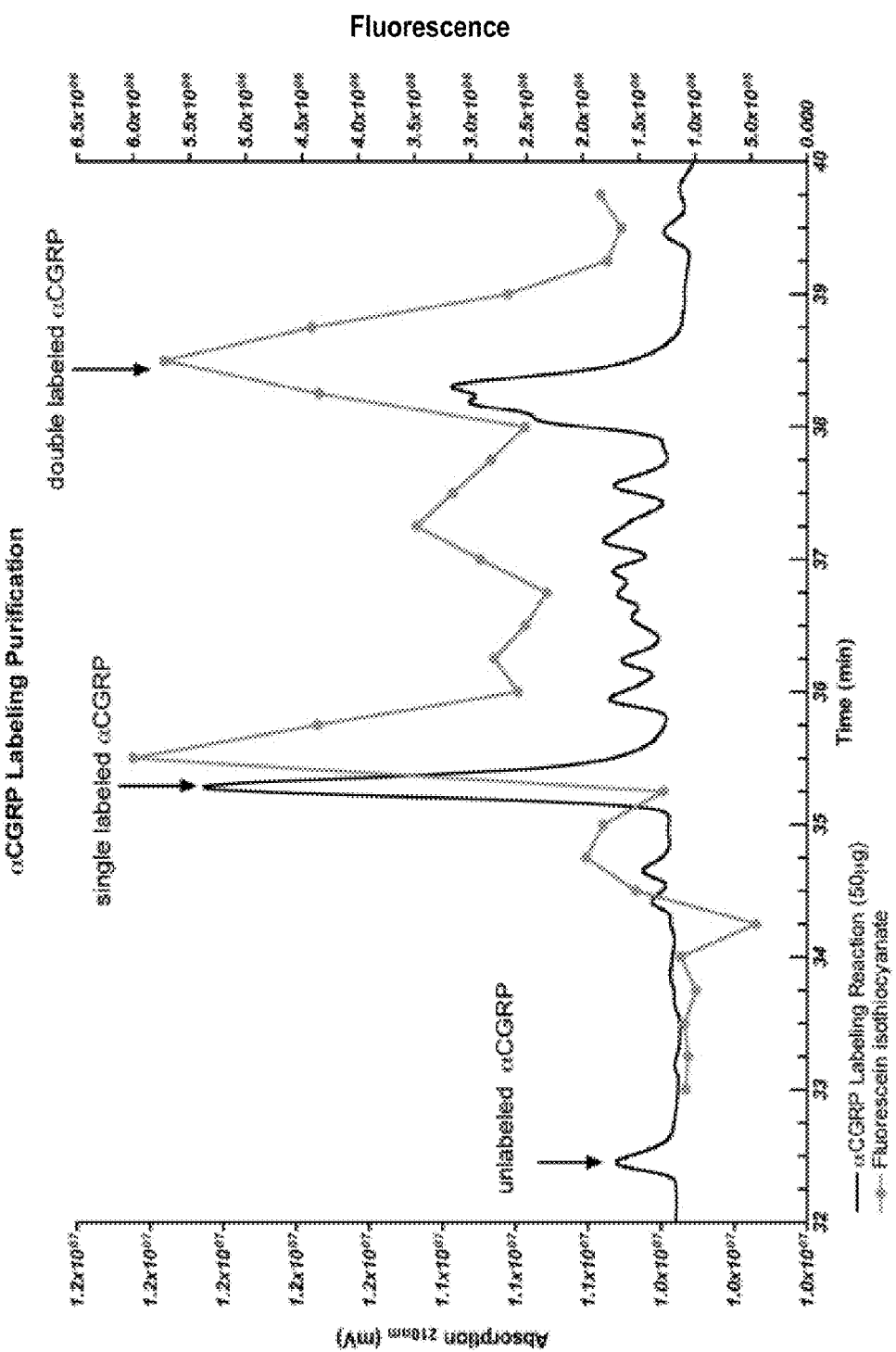

Two fluorescent forms of CGRP were observed, containing single or double fluorescent labels (FIG. 9B). Single-labeled FL-CGRP was identified by Fourier Transform Mass Spectroscopy and by InfraRed Multi-Photon Dissociation at the University of Rochester Proteomics core. The peak identified as single-labeled FL-CGRP (FIG. 9B) was confirmed to contain CGRP with a single dye molecule attached to the lysine$^{24}$ residue.

This process achieved an efficiency of 30% for purification, and produced a pure population of single-labeled FL-CGRP appropriate for development of binding assays for CGRP receptor.

Example 6

Development of Fluorescent Competition Assays for CGRP

To be useful for development of non-radioactive competition assays, which will be useful for quantifying CGRP in tissues and cells, the FL-label at lysine$^{24}$ cannot inhibit anti-CGRP antibody binding. The ability of anti-CGRP antibodies to immunoprecipitate FL-CGRP was assessed first. Using two antibodies raised against rat CGRP, designated JH84 and MU33, an immunoprecipitation assay was performed to assess whether these two antibodies could quantitatively immunoprecipitate FL-CGRP. Both antibodies do, in fact, immunoprecipitate FL-CGRP, and this effect was blocked by the addition of saturating unlabeled CGRP (FIG. 10A). The binding sites for JH84 and MU33 on CGRP are illustrated schematically in FIG. 10B.

Figure 11:
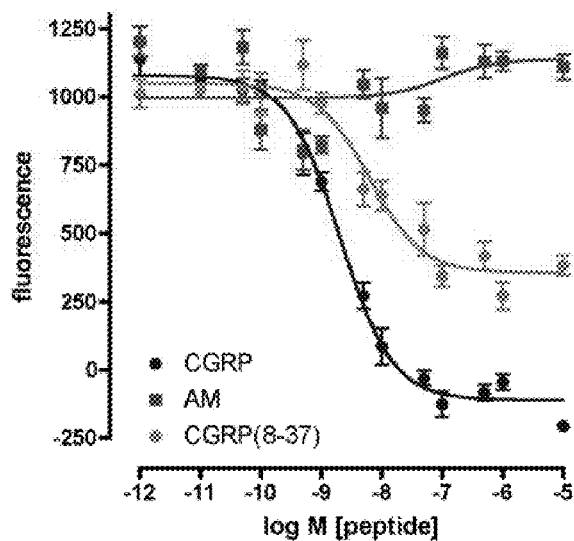
FIG. 11 is a graph illustrating that FL-CGRP can be used for a competition assay to determine CGRP concentrations. Affinity-purified JH84 antibody (100 ng/well) was linked to wells in a 96-well plate, and incubated with 100 pM FL-CGRP and increasing concentrations of unlabeled CGRP. Unbound peptide was washed from well, and fluorescence detected in a Perkin Elmer plate reader.

FL-CGRP was then used to develop a fluorescent competition assay. Affinity-purified anti-CGRP antibody JH84 was bound to the wells of a 96-well plate and 100 µM FL-CGRP was incubated as tracer with either unlabeled CGRP, the homologous neuropeptide adrenomedullin (AM), or the CGRP antagonist CGRP(8-37). CGRP effectively competed with FL-CGRP for binding to immobilized antibody (FIG. 11) and AM did not compete, thereby demonstrating specificity of the assay. The CGRP antagonist partially competed with FL-CGRP, suggesting that some of the polyclonal antibodies used to coat the well were directed against the sequences missing in CGRP(8-37). Thus, the antagonist could not totally compete with FL-CGRP for binding to the antibodies.

The preceding results demonstrate that FL-CGRP is suitable for immunoassays or competition assays.

Example 7

FL-CGRP Binds Specifically to Cells Expressing CGRP Receptors

Figure 12:
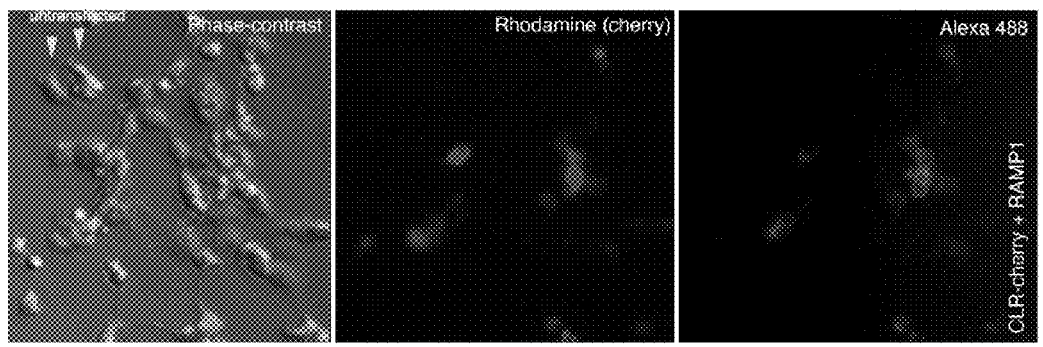
FIG. 12 is a panel of microscopy images illustrating that FL-CGRP specifically binds to cells expressing CLR and RAMP1. COS1 cells were transfected with CLR-cherry and RAMP1. 30 nM FL-CGRP was incubated with transfected cells for 30 minutes, and cells were washed 2× with PBS and visualized by phase-contrast microscopy (left panel), and fluorescent microscopy to identify cells expressing the CLR-cherry fusion protein (center panel) and cells that bound FL-CGRP (right panel).
Figure 13:
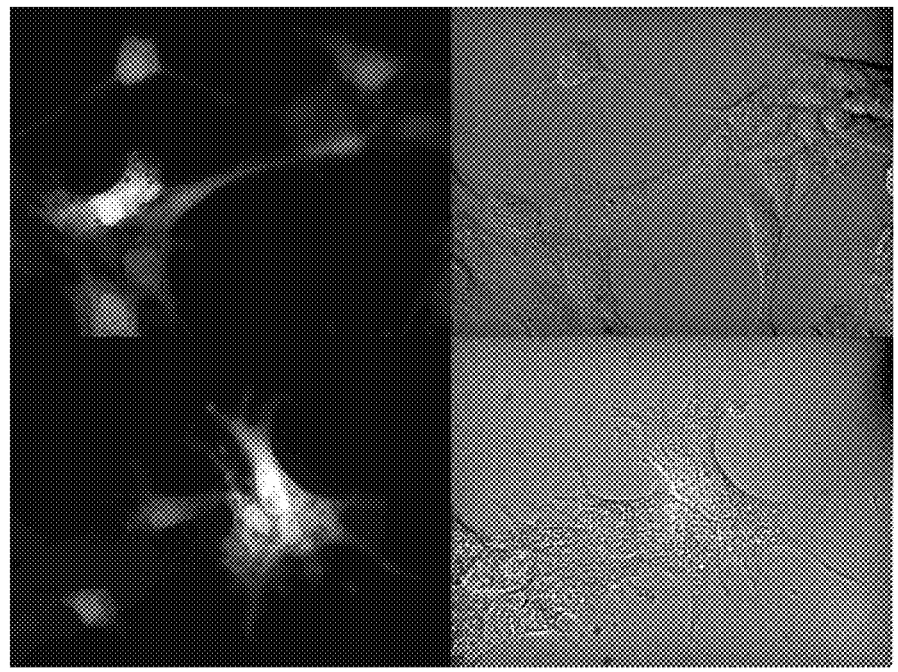
FIG. 13 is a panel of microscopy images illustrating that FL-CGRP binds to CNS1 glioma cells. CNS1 cells were incubated with 30 nM FL-CGRP for 30 minutes, and imaged using phase-contrast microscopy (right, upper and lower panels) and fluorescent microscopy for FL-CGRP (left, upper and lower panels).

COS cells do not endogenously express CGRP receptors. COS1 cells were transfected with a fusion protein containing CLR-fused at its carboxyl terminus to the fluorescent protein cherry. CLR-cherry and RAMP1 were co-transfected into COS1 cells, and 48 hours post-transfection cells were incubated with FL-CGRP, and imaged using phase contrast microscopy (FIG. 12, left panel) as well as fluorescence microscopy for cherry (580 nm) (FIG. 12, center panel) and FL-CGRP (488 nm) (FIG. 12, right panel). FL-CGRP was only observed to bind to cells that were expressing CLR-cherry. No FL-CGRP binding was detected in untransfected cells. Similar binding was observed in CNS1 glioma cells, which express CGRP receptors and responded to CGRP in the proliferation assay (FIG. 13).

Thus, the FL-CGRP ligand can be used for identifying CGRP receptors. FL-CGRP binds to CGRP receptors with high-affinity, and is suitable for identification of cells expressing CGRP receptors in cell culture and in tissue. Purified FL-CGRP represents a new reagent that differs from predecessor fluorophore-labeled CGRP in its high purity (i.e., containing highly pure single-fluorophore labeled CGRP) and high signal. These properties allow for its use in fluorescence-based assays for the CGRP receptors, including analysis by fluorescence activated cell sorting (FACS) and high-throughput screening.

Example 8

High-Throughput Screen for Novel Antagonists of CGRP Receptor

A rapid and sensitive assay for protein-protein interaction has been developed based on polarized fluorescence resonance energy transfer (pFRET). The CGRP receptor components, CLR, RAMP1 and RCP, have been tagged with fluorescent donor/acceptor proteins, and small compound libraries will be screened for molecules that disrupt pFRET between CLR-RAMP1. Since these molecules will be selected for their ability to block protein-protein interactions they will not be limited to classical antagonists that bind the extracellular domain of CLR. It is presumed this group will include hydrophobic molecules that can pass through the cell membranes, and thus may also be candidates for compounds that could pass through the blood-brain barrier.

Preliminary studies indicate that it is necessary to tightly control expression of both donor and acceptor fusion protein to avoid false-positive FRET reactions. Therefore, cell lines that express donor and acceptor pairs will be developed for analysis of CLR proteins by pFRET. If one of the FRET pair does not express well, or if the pair expression is too high or too low, then data interpretation becomes problematic. To avoid this difficulty the Tetracycline-responsive system will be used. RAMP 1-venus and CLR-cerulean fusion proteins will be cloned into the Tet-responsive bidirectional plasmid pTRE-Tight-BI (Clontech). This plasmid uses a tightly regulated bidirectional tetracycline-responsive promoter that will express both constructs with equal efficiency. The resulting plasmid, pTRE-Tight/cpd2$^{CLR}$+RCP, will be co-transfected into COS1 cells with pTet-ON plasmid, which constitutively expresses the reverse tetracycline-controlled transactivator. When both plasmids are expressed in a cell, addition of tetracycline will induce expression of RAMP1-venus and CLR-cerulean. COS1 cells endogenously express RCP and transfect with high efficiency, thus making an ideal cellular environment for HTS.

Stable cell lines will be isolated following geneticin selection, and screened for expression of cerulean and venus by fluorescence microscopy in response to doxycycline. By inducing cells with increasing concentrations of tetracycline, a dose-response curve of protein expression will be generated. pFRET analysis will be carried out by MPLSM using both microscopy and plate reader detection. An example of a control pFRET experiment carried out in the plate reader is shown in FIG. 6, where the interaction between CLR loop 2 and RCP was detected in transient experiments. Control cell lines that substitute free cerulean for RCP-cerulean will be made and used as an initial negative control. Tetracycline conditions that give sufficient levels of expression and a high z-score will be optimized (Malo et al., "Statistical Practice in High-Throughput Sreening Data Analysis," *Nat Biotechnol* 24(2):167-75 (2006); Zhang et al., "A Simple Statistical Parameter for Use in Evaluation and Validation of High Throughput Screening Assays," *J Biomol Screen* 4(2):67-73 (1999); Zhang X. D., "A New Method With Flexible and Balanced Control of False Negatives and False Positives for Hit Selection in RNA Interference High-Throughput Screening Assays," *J Biomol Screen* 12(5):645-55 (2007); Zhang et al., "The Use of Strictly Standardized Mean Difference for Hit Selection in Primary RNA Interference High-Throughput Screening Experiments," *J Biomol Screen* 12(4):497-509 (2007), which are hereby incorporated by reference in their entirety), similar to the 0.8 recorded for preliminary experiments.

Identification of novel compounds that disrupt CLR protein interactions will be carried out using the stable cell lines expressing CLR-cerulean+RAMP1-venus. In these experiments compounds that disrupt the pFRET interaction, resulting in increased anisotropy over control, will be identified. Compounds identified in this screening will be subjected to in vivo testing according to Examples 5-8 for efficacy in treating breast cancer, inhibiting breast cancer metastasis, and treating glioma.

Example 9

The Effect of CGRP Inhibition on Breast Cancer Tumor Growth

To test the effect of CGRP inhibition on breast cancer tumor growth, MDA-MB-231 human breast tumor cells will be grown in the mammary fat pad of nude mice. An osmotic pump that will continuously secrete either the peptide inhibitor of CGRPR signaling (CGRP$_{8-37}$, purchased from California Peptide Research, Inc.) or saline as control will be implanted in each mouse. Tumor size will be measured via calipers every two days for two weeks. After two weeks of growth and treatment, tumors will be excised for histology. It is predicted that CGRP$_{8-37}$ treatment will significantly retard tumor growth.

Example 10

The Role of CGRP in Breast Cancer Metastasis to the Brain

An in vivo model will be employed to determine whether inhibition of CGRP receptor signaling can prevent breast cancer metastasis. In this model, the MDA-MB231 and MDA-MB-231BR cell lines expressing the Tet-repressible dominant negative CLR inhibitor L2-EGFP (MDA-MB-231/L2-EGFP and MDA-MB-231BR/L2-EGFP) or GFP alone (MDA-MB-231BR/GFP and MDA-MB-231/GFP), as described in Example 3, will be suspended (2×10$^5$ cells) in 10 µl of Dulbecco's PBS with 0.5% FBS for intracardial injection into 20 nude mice via a stereotactic frame. Three weeks later animals will be perfusion fixed, and brain, lungs, ovaries, femurs and adrenal glands will be dissected. Organs will be paraffin embedded and sectioned (bones will undergo decalcification in 14% EDTA for two weeks) and the number and size of micrometastases will be quantified systemically on an epifluorescence microscope (Yoneda et al., "A Bone-Seeking Clone Exhibits Different Biological Properties From the MDA-MB-231 Parental Human Breast Cancer Cells and A Brain-Seeking Clone In Vivo and In Vitro," *J Bone Miner Res* 16(8):1486-95 (2001), which is hereby incorporated by reference in its entirety). This particular intracardiac injection model allows for examining only the later stages of metastasis, after cells have entered the bloodstream. It is these later stages where it is believed that CGRP signaling plays a role in the metastatic process.

Figure 14:
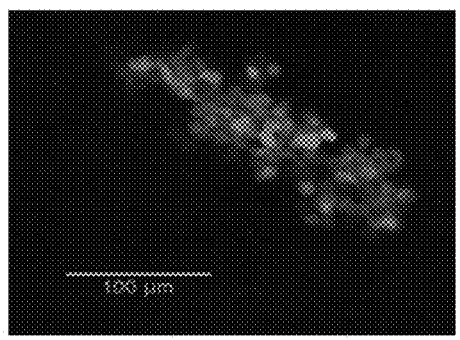
FIG. 14 is a fluorescent photomicrograph visualizing the metastasis of MDA-MB231BR/GFP-labeled cells to the brain following intracardiac injection. MDA-MB-231 BR cells were stably transfected with GFP, and geneticin-resistant colonies were isolated and characterized. Fluorescent breast cancer cells were then injected intracardially and formed a brain metastasis within 21-days post injection.

FIG. 14 is a fluorescent photomicrograph showing visualization of a MDA-MB-231BR/GFP brain metastasis in a nude mouse 21-days after intracardiac injection of the cells. Seventy-two 50 µm sections of the brain were inspected per animal and twenty-six +/−6 tumors were observed per animal, with tumors appearing primarily in cortex, cerebellum and brain stem. In contrast, no brain tumors were observed when MDA-MB-231/GFP cells were similarly injected into mice. This same form of analysis will be performed on the treated mice.

In addition to CLR-dominant negative inhibition of CGRP mediated signaling, non-peptide CGRP antagonists will also be tested in the intracardiac injection model for their ability to inhibit breast cancer cell brain metastasis. There are currently two non-peptide CGRP antagonists available: BIBN4096BS (Doods et al., "CGRP Antagonists: Unravelling the Role of CGRP in Migraine," *Trends Pharmacol Sci* 28(11):580-7 (2007); Edvinsson L., "Clinical Data on the CGRP Antagonist BIBN4096BS for Treatment of Migraine Attacks," *CNS Drug Rev* 11(1):69-76 (2005); and Olesen et al., "Calcitonin Gene-Related Peptide Receptor Antagonist BIBN 4096 BS for the Acute Treatment of Migraine," *N Engl J Med* 350(11): 1104-10 (2004), which are hereby incorporated by reference in their entirety), and MK-0974 (Salvatore et al., "Pharmacological Characterization of MK-0974, A Potent and Orally Active CGRP Receptor Antagonist for the Treatment of Migraine," *J Pharmacol Exp Ther* (2007) and Ho et al., "Randomized Controlled Trial of an Oral CGRP Antagonist, MK-0974, in Acute Treatment of Migraine," *Neurology* (2007), which are hereby incorporated by reference in their entirety).

In these studies, MDA-MB-231BR/GFP cells (brain-metastasizing) and MDA-MB-231/GFP cells (non-brain metastasizing) will be injected intracardially into nude mice via a stereotactic frame. For each cell type two therapeutic strategies will be evaluated. In the first strategy, treatment with CGRP antagonist will begin three days before injection with tumor cells, and treatment will continue throughout the subsequent three weeks until animal sacrifice. In the second strategy, treatment with CGRP antagonist will only begin one week after animals are injected with tumor cells, and treatment will continue for the subsequent two weeks until animal sacrifice. The first regimen provides the CGRP antagonists with the greatest opportunity to influence every step of the metastatic process, while the second regimen will evaluate CGRP antagonist efficacy after metastases have already established. BIB4096 has 100-1000× lower affinity for rodent receptors over human receptors, and are not usually amenable to rodent studies (Mallee et al., "Receptor Activity-Modifying Protein 1 Determines the Species Selectivity of Non-Peptide CGRP Receptor Antagonists," *J Biol Chem* 277(16): 14294-8 (2002) and Hershey et al., "Investigation of the Species Selectivity of A Nonpeptide CGRP Receptor Antagonist Using A Novel Pharmacodynamic Assay," *Regul Pept* 127(1-3):71-7 (2005), which are hereby incorporated by reference in their entirety). However, MDA-MB-231 cells are human and, therefore, will allow for monitoring human CGRP receptor pharmacology in the mouse background. Antagonists will be delivered by an Alzet mini-osmotic pump. Antagonists have been used at doses of 30-300 µg/kg in monkeys (Hershey et al., "Investigation of the Species Selectivity of A Nonpeptide CGRP Receptor Antagonist Using A Novel Pharmacodynamic Assay," *Regul Pept* 127(1-3):71-7 (2005), which is hereby incorporated by reference in its entirety). Starting doses of 150 µg/kg will be used, although depending on the initial results doses of 50 µg/kg and 300 µg/kg will also be assessed.

For these experiments, mice will be approximately 20 grams at the time of surgery and the Alzet #2004 pump has the appropriate delivery rate (0.25 µl/hr for up to 4 weeks, 200 µl capacity) for antagonist. Pumps will be implanted subcutaneously in the back, and antagonist delivered to the vasculature via catheter to the external jugular (Menon et al., "Angiotensin-(1-7) Inhibits Growth of Human Lung Adenocarcinoma Xenografts in Nude Mice Through A Reduction in Cyclooxygenase-2," *Cancer Res* 67(6):2809-15 (2007), which is hereby incorporated by reference in its entirety). After perfusion fixation brain, femurs, ovaries, and adrenal glands will be prepared and analyzed for metastases. If no change in brain metastasis is observed at the 150 µg/kg dose, the dose will be increased. Conversely, if a diminution in fluorescent brain metastasis is observed, the dosing will be decreased to discover the lower limits of antagonist activity.

Example 11

The Effect of CGRP Peptide Inhibition on Glioma Tumor Growth

CNS-1 (rat glioma) tumors will be grown subcutaneously in the flank of nude mice. An osmotic pump that continuously secretes either the peptide inhibitor of CGRPR signaling (CGRP$_{8-37}$) or saline as control will be implanted in each mouse. Tumor size will be measured via calipers every two days for two weeks. After two weeks of growth and treatment, tumors will be excised for histology. It is predicted that CGRP$_{8-37}$ treatment significantly retards tumor growth.

Example 12

The Role of CLR in Glioma Proliferation in an In Vivo Model

Because constitutive expression of L2-EGFP completely inhibited glioma growth, the use of a tetracycline-repressible promoter will be used to inhibit expression of L2-EGFP in CNS1 cells during culturing as described in Example 3.

Figure 15:
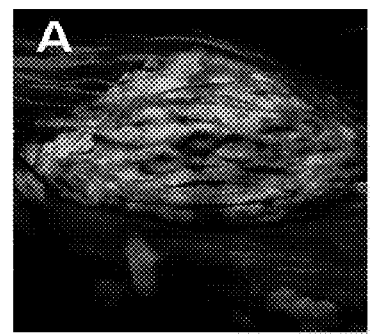
FIG. 15 is a fluorescent photomicrograph of glioma cells visualized with multi-photon laser-scanning microscropy (MPLSM) in live animals. U87 glioma cells expressing GFP were implanted into cranial window and imaged 14-days later. Vasculature is also imaged by injection of tetramethyl-rhodamine dextran in tail vein.

Glioma cells expressing the L2-EGFP dominant-negative inhibitor of CLR signaling or GFP alone will be stereotactically injected into the cortex of severe combined immunodeficiency (SCID) mice approximately 200 µm deep. To image glioma tumor cell proliferation in the cortex, a cranial window (Brown et al., *A Practical Guide: In vivo Imaging of Tumors*, in *Imaging in Neuroscience and Development*, Yuste, Eds., Cold Spring Harbor Laboratory Press: Cold Spring Harbor, N.Y. 695-700 (2005), which is hereby incorporated by reference in its entirety) will be surgically implanted in the skull of the animal, allowing repeated optical access to visualize expression of the L2-EGFP fusion protein and monitor changes in tumor cell proliferation and angiogenesis by multi-photon laser-scanning microscopy (MPLSM). MPLSM allows non-invasive 3D visualization of the tumor to a depth of 500 µm below the tissue surface (Brown et al., "In Vivo Measurement of Gene Expression, Angiogenesis and Physiological Function in Tumors Using Multiphoton Laser Scanning Microscopy," *Nat Med* 7(7):864-8 (2001), which is hereby incorporated by reference in its entirety). FIG. 15 shows human U87 glioma cells transfected with GFP alone visualized with MPLSM in live animals 14-days after implantation. Tumor cells will be assessed for proliferation over three weeks, and tumor growth tracked by measuring the volume of the cranial window occupied by fluorescent tumor tissue. It is expected that CNS1 glioma cells that express L2-EGFP will have decreased proliferation rates compared to control CNS1 cells.

All of the features described herein (including any accompanying claims, abstract and drawings), and/or all of the steps of any method or process so disclosed, may be combined with any of the above aspects in any combination, except combinations where at least some of such features and/or steps are mutually exclusive. Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed:

1. A method of inhibiting survival of a metastatic cancer cell or inhibiting establishment of a cancerous metastasis comprising:

contacting a metastatic cancer cell in vivo with a calcitonin-gene related peptide ("CGRP") receptor antagonist, $CGRP_{8-37}$, wherein said contacting is effective to inhibit CGRP receptor activity and either kill or inhibit growth of the metastatic cancer cell or inhibit establishment of a cancerous metastasis.

2. The method according to claim 1, wherein the cancer is selected from breast, ovarian, prostate, liver, lung, colon, stomach, esophageal, glioma, or melanoma.

3. The method according to claim 1, wherein said contacting is carried out by administering the agent to a patient having at least one primary tumor.

* * * * *

SEQUENCE LISTING

```
<160> NUMBER OF SEQ ID NOS: 10

<210> SEQ ID NO 1
<211> LENGTH: 111
<212> TYPE: DNA
<213> ORGANISM: Homo sapiens

<400> SEQUENCE: 1
gcctgtgaca ctgccacctg tgtgactcat cggctggcgg gcttgctgag cagatcaggg      60
ggtgtggtga agaacaactt tgtgcccacc aatgtgggtt ccaaagcctt c             111

<210> SEQ ID NO 2
<211> LENGTH: 37
<212> TYPE: PRT
<213> ORGANISM: Homo sapiens

<400> SEQUENCE: 2

Ala Cys Asp Thr Ala Thr Cys Val Thr His Arg Leu Ala Gly Leu Leu
```

```
1               5                  10                 15
Ser Arg Ser Gly Gly Val Val Lys Asn Asn Phe Val Pro Thr Asn Val
            20                  25                  30

Gly Ser Lys Ala Phe
        35

<210> SEQ ID NO 3
<211> LENGTH: 447
<212> TYPE: DNA
<213> ORGANISM: Homo sapiens

<400> SEQUENCE: 3
atggcccggg ccctgtgccg cctcccgcgg cgcggcctct ggctgctcct ggcccatcac      60
ctcttcatga ccactgcctg ccaggaggct aactacggtg ccctcctccg ggagctctgc     120
ctcacccagt tccaggtaga catggaggcc gtcggggaga cgctgtggtg tgactggggc     180
aggaccatca ggagctacag ggagctggcc gactgcacct ggcacatggc ggagaagctg     240
ggctgcttct ggcccaatgc agaggtggac aggttcttcc tggcagtgca tggccgctac     300
ttcaggagct gccccatctc aggcagggcc gtgcgggacc cgcccggcag catcctctac     360
cccttcatcg tggtccccat cacggtgacc ctgctggtga cggcactggt ggtctggcag     420
agcaagcgca ctgagggcat tgtgtag                                         447

<210> SEQ ID NO 4
<211> LENGTH: 148
<212> TYPE: PRT
<213> ORGANISM: Homo sapiens

<400> SEQUENCE: 4

Met Ala Arg Ala Leu Cys Arg Leu Pro Arg Arg Gly Leu Trp Leu Leu
1               5                  10                 15

Leu Ala His His Leu Phe Met Thr Thr Ala Cys Gln Glu Ala Asn Tyr
            20                  25                  30

Gly Ala Leu Leu Arg Glu Leu Cys Leu Thr Gln Phe Gln Val Asp Met
        35                  40                  45

Glu Ala Val Gly Glu Thr Leu Trp Cys Asp Trp Gly Arg Thr Ile Arg
    50                  55                  60

Ser Tyr Arg Glu Leu Ala Asp Cys Thr Trp His Met Ala Glu Lys Leu
65                  70                  75                  80

Gly Cys Phe Trp Pro Asn Ala Glu Val Asp Arg Phe Phe Leu Ala Val
                85                  90                  95

His Gly Arg Tyr Phe Arg Ser Cys Pro Ile Ser Gly Arg Ala Val Arg
            100                 105                 110

Asp Pro Pro Gly Ser Ile Leu Tyr Pro Phe Ile Val Val Pro Ile Thr
        115                 120                 125

Val Thr Leu Leu Val Thr Ala Leu Val Val Trp Gln Ser Lys Arg Thr
    130                 135                 140

Glu Gly Ile Val
145

<210> SEQ ID NO 5
<211> LENGTH: 1386
<212> TYPE: DNA
<213> ORGANISM: Homo sapiens

<400> SEQUENCE: 5
atggagaaaa agtgtaccct gtatttctg gttctcttgc cttttttat gattcttgtt       60
```

```
acagcagaat tagaagagag tcctgaggac tcaattcagt tgggagttac tagaaataaa       120
atcatgacag ctcaatatga atgttaccaa aagattatgc aagaccccat caacaagca        180 gaaggcgttt actgcaacag aacctgggat ggatggctct gctggaacga tgttgcagca      240
ggaactgaat caatgcagct ctgccctgat tactttcagg actttgatcc atcagaaaaa      300
gttacaaaga tctgtgacca agatggaaac tggtttagac atccagcaag caacagaaca      360
tggacaaatt atacccagtg taatgttaac acccacgaga aagtgaagac tgcactaaat      420
ttgttttacc tgaccataat tggacacgga ttgtctattg catcactgct tatctcgctt      480
ggcatattct tttatttcaa gagcctaagt tgccaaagga ttccttaca caaaaatctg        540 ttcttctcat ttgtttgtaa ctctgttgta acaatcattc acctcactgc agtggccaac      600
aaccaggcct tagtagccac aaatcctgtt agttgcaaag tgtcccagtt cattcatctt      660
tacctgatgg gctgtaatta cttttggatg ctctgtgaag gcatttaccct acacacactc      720 attgtggtgg ccgtgtttgc agagaagcaa catttaatgt ggtattattt tcttggctgg      780
ggatttccac tgattcctgc ttgtatacat gccattgcta aagcttata ttacaatgac        840 aattgctgga tcagttctga tacccatctc ctctacatta tccatggccc aatttgtgct      900
gctttactgg tgaatctttt tttcttgtta aatattgtac gcgttctcat caccaagtta      960
aaagttacac accaagcgga atccaatctg tacatgaaag ctgtgagagc tactcttatc     1020
ttggtgccat tgcttggcat tgaatttgtg ctgattccat ggcgacctga aggaaagatt     1080
gcagaggagg tatatgacta catcatgcac atccttatgc acttccaggg tcttttggtc     1140
tctaccattt tctgcttctt taatggagag gttcaagcaa ttctgagaag aaactggaat     1200
caatacaaaa tccaatttgg aaacagcttt tccaactcag aagctcttcg tagtgcgtct     1260
tacacagtgt caacaatcag tgatggtcca ggttatagtc atgactgtcc tagtgaacac     1320
ttaaatggaa aaagcatcca tgatattgaa aatgttctct taaaaccaga aaatttatat     1380
aattga                                                                1386
```

<210> SEQ ID NO 6
<211> LENGTH: 461
<212> TYPE: PRT
<213> ORGANISM: Homo sapiens

<400> SEQUENCE: 6

```
Met Glu Lys Lys Cys Thr Leu Tyr Phe Leu Val Leu Leu Pro Phe Phe
1               5                   10                  15

Met Ile Leu Val Thr Ala Glu Leu Glu Ser Pro Glu Asp Ser Ile
        20                  25                  30

Gln Leu Gly Val Thr Arg Asn Lys Ile Met Thr Ala Gln Tyr Glu Cys
    35                  40                  45

Tyr Gln Lys Ile Met Gln Asp Pro Ile Gln Gln Ala Glu Gly Val Tyr
50                  55                  60

Cys Asn Arg Thr Trp Asp Gly Trp Leu Cys Trp Asn Asp Val Ala Ala
65                  70                  75                  80

Gly Thr Glu Ser Met Gln Leu Cys Pro Asp Tyr Phe Gln Asp Phe Asp
                85                  90                  95

Pro Ser Glu Lys Val Thr Lys Ile Cys Asp Gln Asp Gly Asn Trp Phe
            100                 105                 110

Arg His Pro Ala Ser Asn Arg Thr Trp Thr Asn Tyr Thr Gln Cys Asn
        115                 120                 125

Val Asn Thr His Glu Lys Val Lys Thr Ala Leu Asn Leu Phe Tyr Leu
    130                 135                 140
```

```
Thr Ile Ile Gly His Gly Leu Ser Ile Ala Ser Leu Leu Ile Ser Leu
145                 150                 155                 160

Gly Ile Phe Phe Tyr Phe Lys Ser Leu Ser Cys Gln Arg Ile Thr Leu
                165                 170                 175

His Lys Asn Leu Phe Phe Ser Phe Val Cys Asn Ser Val Val Thr Ile
            180                 185                 190

Ile His Leu Thr Ala Val Ala Asn Asn Gln Ala Leu Val Ala Thr Asn
        195                 200                 205

Pro Val Ser Cys Lys Val Ser Gln Phe Ile His Leu Tyr Leu Met Gly
    210                 215                 220

Cys Asn Tyr Phe Trp Met Leu Cys Glu Gly Ile Tyr Leu His Thr Leu
225                 230                 235                 240

Ile Val Val Ala Val Phe Ala Glu Lys Gln His Leu Met Trp Tyr Tyr
                245                 250                 255

Phe Leu Gly Trp Gly Phe Pro Leu Ile Pro Ala Cys Ile His Ala Ile
                260                 265                 270

Ala Arg Ser Leu Tyr Tyr Asn Asp Asn Cys Trp Ile Ser Ser Asp Thr
            275                 280                 285

His Leu Leu Tyr Ile Ile His Gly Pro Ile Cys Ala Ala Leu Leu Val
    290                 295                 300

Asn Leu Phe Phe Leu Leu Asn Ile Val Arg Val Leu Ile Thr Lys Leu
305                 310                 315                 320

Lys Val Thr His Gln Ala Glu Ser Asn Leu Tyr Met Lys Ala Val Arg
                325                 330                 335

Ala Thr Leu Ile Leu Val Pro Leu Leu Gly Ile Glu Phe Val Leu Ile
                340                 345                 350

Pro Trp Arg Pro Glu Gly Lys Ile Ala Glu Val Tyr Asp Tyr Ile
            355                 360                 365

Met His Ile Leu Met His Phe Gln Gly Leu Leu Val Ser Thr Ile Phe
    370                 375                 380

Cys Phe Phe Asn Gly Glu Val Gln Ala Ile Leu Arg Arg Asn Trp Asn
385                 390                 395                 400

Gln Tyr Lys Ile Gln Phe Gly Asn Ser Phe Ser Asn Ser Glu Ala Leu
                405                 410                 415

Arg Ser Ala Ser Tyr Thr Val Ser Thr Ile Ser Asp Gly Pro Gly Tyr
            420                 425                 430

Ser His Asp Cys Pro Ser Glu His Leu Asn Gly Lys Ser Ile His Asp
    435                 440                 445

Ile Glu Asn Val Leu Leu Lys Pro Glu Asn Leu Tyr Asn
450                 455                 460

<210> SEQ ID NO 7
<211> LENGTH: 447
<212> TYPE: DNA
<213> ORGANISM: Homo sapiens

<400> SEQUENCE: 7
atggaagtga aggatgccaa ttctgcgctt ctcagtaact acgaggtatt tcagttacta      60
actgatctga agagcagcg taaagaaagt ggaagaata acacagctc tgggcaacag        120 aacttgaaca ctatcaccta tgaaacgtta aatacatat caaaacacc atgcaggcac       180 cagagtcctg aaattgtcag agaatttctc acagcattga aagccacaa gttgaccaaa      240 gctgagaagc tccagctgct gaaccaccgg cctgtgactg ctgtggagat ccagctgatg     300
gtggaagaga gtgaagagcg gctcacggag gagcagattg aagctcttct ccacaccgtc     360
```

-continued accagcattc tgcctgcaga gccagaggct gagcagaaga agaatacaaa cagcaatgtg    420
gcaatggacg aagaggaccc agcatag    447

<210> SEQ ID NO 8
<211> LENGTH: 148
<212> TYPE: PRT
<213> ORGANISM: Homo sapiens

<400> SEQUENCE: 8

Met Glu Val Lys Asp Ala Asn Ser Ala Leu Leu Ser Asn Tyr Glu Val
1               5                   10                  15

Phe Gln Leu Leu Thr Asp Leu Lys Glu Gln Arg Lys Glu Ser Gly Lys
                20                  25                  30

Asn Lys His Ser Ser Gly Gln Gln Asn Leu Asn Thr Ile Thr Tyr Glu
            35                  40                  45

Thr Leu Lys Tyr Ile Ser Lys Thr Pro Cys Arg His Gln Ser Pro Glu
        50                  55                  60

Ile Val Arg Glu Phe Leu Thr Ala Leu Lys Ser His Lys Leu Thr Lys
65                  70                  75                  80

Ala Glu Lys Leu Gln Leu Leu Asn His Arg Pro Val Thr Ala Val Glu
                85                  90                  95

Ile Gln Leu Met Val Glu Glu Ser Glu Glu Arg Leu Thr Glu Glu Gln
            100                 105                 110

Ile Glu Ala Leu Leu His Thr Val Thr Ser Ile Leu Pro Ala Glu Pro
        115                 120                 125

Glu Ala Glu Gln Lys Lys Asn Thr Asn Ser Asn Val Ala Met Asp Glu
    130                 135                 140

Glu Asp Pro Ala
145

<210> SEQ ID NO 9
<211> LENGTH: 31
<212> TYPE: DNA
<213> ORGANISM: artificial
<220> FEATURE:
<223> OTHER INFORMATION: antisense inhibitor of CGRP receptor function

<400> SEQUENCE: 9
tgctcactgt gtaagcctta aatccatcaa g    31

<210> SEQ ID NO 10
<211> LENGTH: 37
<212> TYPE: PRT
<213> ORGANISM: Rattus norvegicus

<400> SEQUENCE: 10

Ser Cys Asn Thr Ala Thr Cys Val Thr His Arg Leu Ala Gly Leu Leu
1               5                   10                  15

Ser Arg Ser Gly Gly Val Val Lys Asp Asn Phe Val Pro Thr Asn Val
                20                  25                  30

Gly Ser Glu Ala Phe
            35